US009170263B2

(12) United States Patent
Lemoine et al.

(10) Patent No.: US 9,170,263 B2
(45) Date of Patent: Oct. 27, 2015

(54) METHOD FOR QUANTIFYING PROTEINS BY MASS SPECTROMETRY

(75) Inventors: Jérôme Lemoine, Lucenay (FR); Arnaud Salvador, L'Ile d'Abeau (FR); Jean-Philippe Charrier, Tassin la Demi Lune (FR); Tanguy Fortin, Bourgoin Jailleu (FR)

(73) Assignees: bioMerieux, L'Etoile (FR); UNIVERSITE CLAUDE BERNARD LYON I, Villeurbanne (FR); CENTRE NATIONAL DE LA RECHERCHE SCIENTIFIQUE, Paris ( * ) Notice: Subject to any disclaimer, the term of this patent is extended or adjusted under 35 U.S.C. 154(b) by 0 days.

(21) Appl. No.: 13/322,173

(22) PCT Filed: May 21, 2010

(86) PCT No.: PCT/FR2010/050991
§ 371 (c)(1),
(2), (4) Date: Jan. 30, 2012

(87) PCT Pub. No.: WO2010/136706
PCT Pub. Date: Dec. 2, 2010

(65) Prior Publication Data
US 2012/0208224 A1 Aug. 16, 2012

(30) Foreign Application Priority Data
May 29, 2009 (FR) ...................... 09 53576

(51) Int. Cl.
C12Q 1/34 (2006.01)
C12Q 1/37 (2006.01)
H01J 49/00 (2006.01)
G01N 33/68 (2006.01)

(52) U.S. Cl.
CPC ................. *G01N 33/6848* (2013.01)

(58) Field of Classification Search
None
See application file for complete search history.

(56) References Cited

U.S. PATENT DOCUMENTS

| 2004/0072251 | A1 | 4/2004 | Anderson |
| 2004/0229283 | A1 | 11/2004 | Gygi et al. |

FOREIGN PATENT DOCUMENTS

| WO | 2005/098071 | 10/2005 |
| WO | 2006/128492 | 12/2006 |
| WO | 2008/066629 | 6/2008 |
| WO | 2008/145763 | 12/2008 |
| WO | 2009/141310 | 11/2009 |

OTHER PUBLICATIONS

T. Fortin et al., "Multiple Reaction . . . Human Serum", Xp-002566821, Anal. Chem. 2008, 9343-9352.

L. Anderson et al., "Mass Spectrometric . . . Anti-peptide Antibodies SISCAPA", J. Proteome Res., 2004, 235-234.
J. Sherman et al., "How Specific . . . ion redundancy", Proteomics, 2008, 9:1120-1123.
M. Duncan et al., "Quantifying . . . the problem", Proteomics, 2009, 9:1124-1127.
J. Niessen et al., "Human platelets . . . for atorvastatin", MCP, 23 fevrier 2009 E Pub.
A. Izrael-Tomasevic et al., "Targeting Interferon . . . Biological Matrices", Journal of Proteome Research, Apr. 7, 2009 XP-002566819.
Brun et al., "Isotope-labeled Protein Standards", MCP, 2007, 2139-2149.
Sun et al., "Reduction-Alkylation . . . Antibody Disulfides", Bioconjug, Chem. 2005, 16(5) 1282-1290.
B. Herbert et al., "Reduction and . . . and how?", Electrophoresis, 2001, 22: 2046-2057.
J. Stal-Zeng et al., "High sensitivity . . . N-Glycosites", MCP , 2007, 1809-1817.
J. Pratt et al., "Multiplexed absolute . . . QconCAT genes", Nat. Protoc. 2006, 1: 1029-1043.
A. Savitzky et al., "Smoothing and . . . Squares Procedures", 1964, Analytical Chemistry, 36: 1627-1639.
M. Bradford, "A rapid . . . Protein-Dye Binding", Anal. Biochem., 1976, 72: 248-254.
T. Fortin et al., "Clinical Quantitation . . . ELISA Tests", MCP, 2008 E-pub.
L. Anderson & C. Hunger, "Quantitative Mass . . . Plasma Proteins", MCP, 2006, 573-588.
H. Zhang et al., "Mass Spectrometric . . . in Plasma", MCP, 2007, 64-71.
S. Carr et al., "Protein Quantitation . . . Biomarker Purgatory?", Clinical Chemistry, 2008, 1749-1752.
S. Gaskell, "Electrospray: Principles and Practices", J. Mass Spectrom (1997), 32, 677-688.
B. Han et al., "Proteomics: from . . . mass spectrometers", Brief Funct Genomic Proteomic, Sep. 7, 2008, (5) 340-354.
K.Y. Wang et al., "Multiplexed Immunoassay: . . . MALDI-TOF MS", Anal Chem, 2008, 80(16), 6159-6167.
V. Fusaro et a., "Prediction of . . . mass spectrometry", Nature Biotech, 27, 2009; 190-198.
J. Mead et al., "MRMaid, the . . . (MRM) Transitions", MCP, 15, Nov. 2008, E-PUB.
F. Desiere et al., "The PeptideAtlas Project", Nucleic Acids Res. Jan. 1, 2006, 34(database issue) :D655-8.
H. Keshishian et al., "Quatitative, Multiplexed . . . Isotope Dilution", MCP, 2007, 2212-2229.
V. Kulasingam et al., "Product Ion . . . Ion-Trap", J. Proteome Res., 2008, 640-647.

*Primary Examiner* — David J Steadman
*Assistant Examiner* — Paul Holland
(74) *Attorney, Agent, or Firm* — Clark & Brody

(57) ABSTRACT

The present invention relates to a method for the quantitative detection of a target protein in a sample, in which the second-generation fragment ions are detected for providing a series of quantitative measurements, at least one of which is correlated to the amount of proteotypic peptide generated and to the amount of target protein in the sample, characterized in that the selected first-generation fragment ion having a mass $(m/z)_2$ is a doubly-charged peptide having a proline and/or a histidine in position 1.

10 Claims, 9 Drawing Sheets

METHOD FOR QUANTIFYING PROTEINS BY MASS SPECTROMETRY

The present invention relates to the technical field of the quantitative assaying of proteins. In particular, the present invention relates to a novel method for the quantitative assaying of protein by mass spectrometry.

Many techniques for the quantitative assaying of proteins have been developed, the assaying of proteins in complex fluids such as blood samples (serum, plasma) from patients being of essential importance in diagnosis. ELISAs (enzyme-linked immunosorbent assays) are the most widely used at the current time. Among the various known ELISA techniques, the sandwich reaction is the most widely used. It requires two antibodies for the protein of interest, one being bound to the enzyme. More recently, the quantitative assaying of proteins, via their proteotypic peptides, by mass spectrometry techniques such as SRM (Selected Reaction Monitoring) or MRM (Multiple Reaction Monitoring) when several SRM assays are carried out simultaneously, has been validated, in complex fluids, by the applicant (T. Fortin et al., MCP, 2008 E-pub) and others (L. Anderson & C. Hunter, MCP, 2006, 573-588; H. Zhang et al., MCP, 2007, 64-71). Upstream of the assaying by mass spectrometry, the proteins to be assayed are digested, by means of an enzyme, in order to fragment the proteins into peptides. The peptides specific for the protein, called proteotypic peptides, are then assayed by mass spectrometry.

The advantage of assays by SRM or MRM compared with ELISA assays is a considerable reduction in cost and in the time taken to develop the assay, in particular if antibodies required for the ELISA assay must be developed. Such mass spectrometry techniques therefore appear to be methods of choice for assaying proteins, and would make it possible, for example, to validate more simply and more rapidly the clinical advantage of assaying the numerous proteins identified as potential markers by research in proteomic analysis (S. Carr & L. Anderson, Clin. Cem. 2008, 1749-1752).

In the case of an MRM assay, in a triple quadrupole mass spectrometer, particularly suitable for the MRM mode, the proteotypic peptides are quantified according to the principle detailed hereinafter. First of all, the sample containing the peptides to be assayed is introduced into an ionization source, where the peptides are ionized in the gaseous state and converted into "molecular" ions which correspond to the initial peptides with one, two or even three additional protons and therefore carry one, two or even three charges. By virtue of an electrospray-type source, for example, the peptides are ionized while at the same time going from a liquid state to a gaseous state (Gaskell, Electrospray: principles and practise, J. Mass Spectrom. (1997), 32, 677-688). This type of source is particularly suitable when the peptides are separated beforehand by reverse-phase liquid chromatography. Nevertheless, the peptide ionization yield can vary according to the concentration and the nature of the various entities present. This phenomenon is reflected by a matrix effect well known to those skilled in the art. Moreover, it is also possible to ionize the peptides from a solid state by virtue of a MALDI (Matrix Assisted Laser Desorption Ionization) source.

Next, a quadrupole analyzer (Q1) makes it possible to filter the proteotypic peptides according to their mass/charge ratio (m/z). Only peptides having the mass/charge ratio of the proteotypic peptide sought, said ratio being referred to as $(m/z)_1$, are transmitted to the second quadrupole (q2) and play the role of precursor ions for the subsequent fragmentation.

The q2 analyzer makes it possible to fragment the peptides having a mass/charge ratio $(m/z)_1$ into first-generation fragment ions. The fragmentation is generally obtained by collision of the precursor peptides with an inert gas, such as nitrogen or argon.

The first-generation fragment ions are transmitted to a third quadrupole (Q3) which filters the first-generation fragment ions according to a specific mass to charge ratio, said ratio being referred to as $(m/z)_2$. Only the first-generation fragment ions having the mass/charge ratio of a fragment characteristic of the proteotypic peptide sought $(m/z)_2$ are transmitted to the detector in order to be quantified.

This operating mode has a double selectivity, in relation, on the one hand, to the selection of the precursor ion and, on the other hand, to the selection of the first-generation fragment ion. Mass spectrometry in MRM mode is therefore advantageous for the quantification.

The intensity of the current induced by the first-generation fragment ions, measured in the detector, is proportional to the amount of first-generation fragment ions, which is itself proportional to the amount of precursor ions, which is itself proportional to the amount of protein to be assayed. The amount of current measured, induced by the first-generation fragment ions, is therefore directly proportional to the amount of the protein to be assayed. A calibration is nevertheless necessary in order to be able to correlate the area of the peak measured, corresponding to the amount of current induced by the first-generation fragment ions, to the corresponding amount of first-generation fragment ions and, in the end, to the amount of protein to be assayed. The $(nm/z)_1$ and $(m/z)_2$ pairs, called transitions, can be assayed in various mass spectrometer models that can operate in the MRM mode or in the MS/MS (or MS$^2$) mode. By way of example, mention may be made of the models of triple quadrupole type (L. Anderson & C. Hunter, MCP, 2006, 573-588 . . . ), or of ion trap type (B. Han & R. Higgs, Brief Funct Genomic Proteomic. 2008 September; 7(5):340-54), or else of time-of-flight type (MALDI-TOF) (K.-Y. Wang et al., Anal Chem, 2008, 80(16) 6159-6167).

The transitions used to assay a protein must be characteristic of the protein to be assayed and must result in assays that are as sensitive as possible, as specific as possible and as robust as possible in terms of reproducibility and reliability. For this, they must be chosen with great care.

In the methods developed for selecting proteotypic peptides $(m/z)_1$ and $(m/z)_2$, the choice is essentially based on the intensity of the response. For further details, reference may be made to V. Fusaro et al., Nature Biotech. 27; 2009; 190-198. The quality of the peptide separation, upstream of the assay, the amino acid composition, the absence of a precursor peptide that is identical in another protein that may be present and the charge state of the precursor peptide are also factors which are taken into account in the selection. Generally, the masses generated by fragmentation of the precursor ion are measured in the MRM mode or in the MS/MS (MS$^2$) mode. The first-generation fragment ion resulting in the most intense signal is then selected. Next, the precursor-ion fragmentation conditions and the analysis conditions are optimized in order to maximize the signal obtained. It is known that it is favorable to select doubly-charged ions in Q1, and singularly-charged first-generation fragment ions in Q3, preferably having a higher m/z ratio than that of the doubly-charged precursor ion.

Commercial software, such as the MIDAS and MRM Pilot software from Applied Biosystems or else MRMaid (J. Mead et al., MCP, Nov. 15, 2008, E-pub) may be used by those skilled in the art, in order to enable them to predict all the possible transition pairs. They may also make use of a database called PeptideAtlas, constructed by F. Desiere et al.

(Nucleic Acids Res. 2006, Jan. 1; 34(database issue): D655-8) in order to compile all the peptide MRM transitions described by the scientific community. This PeptideAtlas base is available with free access on the Internet.

An alternative approach for selecting the $(m/z)_1$ and $(m/z)_2$ proteotypic peptides consists in using the MS/MS fragmentation spectra obtained on the occasion of other work. This work may be, for example, the phases of discovery and identification of biomarkers by proteomic analysis. This approach was proposed by Thermo Scientific during a meeting of users (J. Mead et al., MCP, Nov. 15, 2008, E-pub). It makes it possible to generate a list of candidate transitions from the peptides identified experimentally by the SIEVE software (Thermo Scientific). Certain criteria have been detailed by J. Mead et al. (MCP, above) for the choice of the $(m/z)_1$ and $(m/z)_2$ ions and are detailed hereinafter:

Peptides with internal cleavage sites, i.e. with internal lysine or arginine, should be avoided, unless the lysine or the arginine is followed by proline, Peptides with asparagine or glutamine should be avoided since they can become deaminated, Peptides with N-terminal glutamine or glutamic acid should be avoided since they can spontaneously cyclize, Peptides with methionine should be avoided since they can be oxidized, Peptides with cysteine should be avoided since they can be nonreproducibly modified during a possible step of denaturation, reduction and blocking of thiol functions, Peptides with proline can be considered to be favorable because they generally produce intense fragments in MS/MS with a single very predominant peak. However, a single very predominant fragment does not make it possible to validate the identity of the transition in a complex mixture. Indeed, only the simultaneous presence of several characteristic fragments makes it possible to verify that the precursor ion sought is indeed detected, Peptides having a proline adjacent to the C-terminal (position n−1) or in the second position relative to the C-terminal (position n−2) are to be avoided since, in this case, the size of the first-generation peptide fragment is generally considered to be too small to be sufficiently specific, The selection of fragments having a mass greater than the precursor is to be favored in order to promote specificity. For this, it is necessary to select a double-charged precursor ion and to select the most intense first-generation fragment ion having a mass greater than the precursor, i.e. a singularly-charged first-generation fragment ion.

Moreover, most commonly, in order to ensure sensitivity and specificity compatible with the assaying of a protein at a concentration of a few ng/ml in a complex fluid (blood, serum, plasma, urine, stool, sputum, etc.), the quantitative assaying by mass spectrometry should be preceded by, in addition to the digestion step, other steps interspersed around the digestion step, for instance:

Phase 1: protein fractionation in order to eliminate the predominant proteins, not corresponding to the protein to be assayed, or else a purification of the sample by any suitable technique: electrophoresis, chromatography, immunocapture (Kulasingam et al., J. Proteome Res., 2008, 640-647). However, the latter technique requires the existence or the preparation of a specific antibody directed against the protein to be assayed, which can be lengthy and expensive to obtain. Furthermore, the subsequent performance levels of the assay by mass spectrometry will be in part linked to the quality and to the specificity of the antibody.

Phase 2: denaturation, reduction and blocking of thiol functions.

Phase 3: digestion.

Phase 4: peptide fractionation.

Phase 2 makes it possible to increase the digestion yield and to ensure better robustness of the assay, in terms of reproducibility and reliability. Phases 1 and 4 are optional when a great sensitivity is not required (L. Anderson & C. Hunter, MCP, above). On the other hand, they are essential when great sensitivity is necessary (a few ng/ml). This is what was demonstrated by T. Fortin et al., above, H. Keshishian et al., MCP, 2007, 2212-2229 and V. Kulasingam et al., J. Proteome Res., 2008, 640-647, L. Anderson et al., J. Proteome Res., 2004, 235-2344 and US 2004/0072251. Indeed, given the precision of the triple quadrupoles in Q1 and Q3, many peptides—isobaric or quasi-isobaric peptides—can generate transitions which are identical or included within the mass tolerances of the instrument (J. Sherman et al., Proteomics, 2008, 9:1120-1123). In this case, the simultaneous injection of a proteotypic peptide and of an isobaric or quasi-isobaric contaminant results in an erroneous quantification through lack of specificity. Separation of the peptides by chromatography upstream of the mass spectrometry provides an additional level of specificity by reducing the number of contaminating peptides (M. Duncan et al., Proteomics, 2009, 9:1124-1127). However, this additional fractionation step may not be sufficient (H. Keshishian et al., above), which makes it necessary to carefully validate any transition used to quantify a protein. In addition, a complete assaying method comprising phases 1, 2 and 4 in addition to the digestion step, in particular when antibodies must be used during phase 1 or 4, is lengthy and expensive.

More recently, a technique known as $MRM^3$ has been implemented for detecting proteins. This technique consists in selecting a first-generation fragment ion, and in subjecting it to a further fragmentation in order to generate second-generation fragment ions. It is then these second-generation fragment ions that are detected. J. Niessen et al. (MCP, Feb. 23, 2009 E-Pub) in particular have used the triplet: precursor/first-generation fragment ion/second-generation fragment ion (called $MRM^3$ transitions) SEQ ID No 1: VLLQTLR (doubly charged)/SEQ ID No 2: LLQTLR (doubly charged)/SEQ ID No 3: LQTLR (singularly charged). However, the authors do not discuss the reasons for choosing this $MRM^3$ transition in particular, and are content with only demonstrating the presence of the target protein, without assaying the latter. More recently, A. Izrael-Tomasevic et al. (Journal of Proteome Research, Targeting Interferon Alpha Subtypes in Serum: A comparison of analytical approaches to the detection and quantitation of proteins in complex biological mixtures, Internet publication date: Apr. 7, 2009) have used $MS^3$ for detecting IFN-alpha, $MS^3$ differing from $MRM^3$ in that the entire $MS^3$ spectrum is used to describe the nature of the proteotypic peptide analyzed. For this, the authors select, for detecting IFN-alpha 4, a molecular ion SEQ ID No 4: HDFGFPQEEFGNQFQK (triply charged) and the ion $y_{15}^{2+}$ SEQ ID No 5: DFGFPQEEFGNQFQK (doubly charged) as first-generation fragment ion which is subjected to a second fragmentation, and also for all the subtypes of IFN-alpha 4, a molecular ion SEQ ID No 6: YSPCAWEVVR (doubly charged) and the ion $y_8^{2+}$ SEQ ID No 7: PCAWEWR (doubly charged) as first-generation fragment ion which is subjected to a second fragmentation. No quantitative assay is carried out either in the $MRM^3$ mode or in the $MS^3$ mode, and the authors emphasize that the ion-trap quantification of IFN-alpha is not satisfactory. The authors note that, even though the signal/noise ratio of the second-generation fragment ions is improved in $MS^3$, the number of counts is at least one thousand times lower than in FT-ICR, and conclude that they favored the SRM (MS2) and AMT (Accurate Mass and Time) (MS without fragmentation) approaches.

In this context, the present invention proposes to provide a novel protein-assay method implementing a mass spectrometry technique which is reliable, easy to implement, and inexpensive. The invention proposes to provide a protein-assay method implementing $MRM^3$ and which is also based on a specific choice of first-generation fragment ions, enabling such a satisfactory quantitative assay.

The invention relates to a method for the quantitative detection of a target protein in a sample, comprising the following steps:
  a) treatment of the sample in order to generate peptides,
  b) quantitative assaying of at least one proteotypic peptide generated from the target protein, via a mass spectrometry technique in which:
    i) the proteotypic peptide is ionized to give precursor ions which are filtered according to their mass m/z, and a given precursor ion having a mass $(m/z)_1$ is selected according to the target protein sought,
    ii) the selected precursor ion is fragmented into first-generation fragment ions,
    iii) the first-generation fragment ions generated are filtered according to their mass m/z, and a given first-generation fragment ion having a mass $(m/z)_2$ is selected according to the target protein sought,
    iv) the selected first-generation fragment ion is fragmented into second-generation fragment ions,
    v) at least a part of the second-generation fragment ions are detected so as to give a series of quantitative measurements,
    vi) at least one quantitative measurement associated with a second-generation fragment ion is selected, and correlated to the amount of proteotypic peptide generated and to the amount of target protein present in the sample,
  characterized in that the selected first-generation fragment ion having a mass $(m/z)_2$ is a doubly-charged peptide which has a proline and/or a histidine in position 1.

The description which follows makes it possible to understand the invention more clearly. By way of introduction, some definitions of the terms used are given below.

The term "peptide" is intended to mean a series of at least two amino acids. The amino acids in question can be natural amino acids, or else modified natural amino acids such as amino acids modified by enzymatic action.

Generally, the term "peptide" is given to a series of from 2 to 100 amino acids. A series of more than 6 amino acids may also be called a "protein", it being impossible for these two notions to be separated by a clear dividing line. In the context of the invention, the term "protein", will denote the amino acid series that are initially present in the sample and the term "peptides" will denote the amino acid series resulting from the cleavage of at least one peptide bond of the initial proteins or of their peptides, for example by digestion, chemical cleavage or fragmentation in a mass spectrometer. The term "protein" includes holoproteins and heteroproteins such as nucleoproteins, lipoproteins, phosphoproteins, metalloproteins and glycoproteins, enzymes, receptors, antibodies and antigens.

The proteins that can be assayed by means of the method of the invention are, in particular, proteins comprising at least one peptide composed of n amino acids, which itself comprises at least one proline in positions 2 to n−2 and/or one histidine in positions 1 to n−2, which will be obtained after cleavage of the initial protein. Preferably, this peptide comprises from 1 to 15 amino acids and at least 6 amino acids.

The term "proteotypic peptide" is intended to mean a peptide generated by treatment of a protein in order to fragment it into peptides, which is characteristic of said protein or of a family of very similar proteins, to which said protein belongs.

The term "sample" is intended to mean any sample capable of containing the protein to be detected. The sample may be of biological origin, i.e. animal, vegetable or human. It may then correspond to a specimen of biological fluid (whole blood, serum, plasma, urine, cephalospinal fluid, organic secretion, for example), a tissue specimen or a specimen of isolated cells. This specimen can be used as it is or can, unless otherwise specified in the description, undergo, prior to the analysis, a preparation of enrichment, extraction, concentration, purification type, according to methods known to those skilled in the art. The sample may be of industrial origin, i.e., according to a nonexhaustive list, a specimen of air, a specimen of water, a specimen taken from a surface, a component or a manufactured product, or a product of food origin. Among the samples of food origin, mention may be made, in a nonexhaustive manner, of a sample of milk products (yoghurts, cheeses), of meat, of fish, of eggs, of fruit, of vegetables, of water or a drink (milk, fruit juice, soda, etc.). These samples of food origin may also come from prepared dishes or sauces. Finally, a food sample may be derived from an animal feed, such as, in particular, animal meals.

The m/z ratio corresponds to the mass to charge ratio of the ionized peptides used in the context of the invention. The terms "mass to charge ratio", "ratio" and even "mass" will be used without distinction to refer to this m/z ratio. The unit of this ratio is in Th, but it may also be given in Da, by extension with its name "mass".

The first step a) of the method according to the invention corresponds to a treatment of the proteins contained in the sample of interest. All of the proteins of the sample are treated in order to fragment the proteins into peptides, for example by digestion with a proteolytic enzyme (protease), or via the action of a chemical reagent. Indeed, the cleavage of the proteins can be carried out by means of a physicochemical treatment, by means of a biological treatment or by means of a combination of the two treatments. Among the treatments that can be used, mention may be made of treatment with hydroxyl radicals, in particular with $H_2O_2$. The treatment with hydroxyl radicals causes a cleavage of the peptide bonds, which takes place randomly on any peptide bond of the protein. The concentration of hydroxyl radicals conditions the number of cleavages carried out and therefore the length of the peptide fragments obtained. Other chemical treatments can also be used, such as, for example, treatment with cyanogen bromide (CNBr) which specifically splits the peptide bonds at the level of the carboxylic group of the methionyl residues. It is also possible to carry out a partial acidic cleavage at the level of the aspartyl residues by heating at 1000° C. a solution of proteins in trifluoroacetic acid.

Treatment of the proteins by enzymatic digestion is nevertheless preferred. Compared with physicochemical treatment, it provides greater preservation of the structure of the proteins, and is easier to control. The term "enzymatic digestion" is intended to mean the simple or combined action of one or more enzymes under suitable reaction conditions. The enzymes performing the proteolysis, called proteases, cleave the proteins at specific sites. Each protease generally recognizes a sequence of amino acids within which it always performs the same cleavage. Certain proteases recognize a single amino acid or a sequence of two amino acids between which they perform a cleavage; other proteases recognize only longer sequences. These proteases may be endoproteases or exoproteases. Among the known proteases, mention may be made, as described in WO2005/098071, of:

specific enzymes, such as trypsin which splits the peptide bond at the carboxylic group of the Arg and Lys residues, endolysin which cleaves the peptide bond of the —CO group of lysines, chymotrypsin which hydrolyzes the peptide bond at the carboxylic group of aromatic residues (Phe, Tyr and Trp), pepsin which cleaves at the $NH_2$ group of aromatic residues (Phe, Tyr and Trp), and the V8 protease of the V8 strain of *Staphylococcus aureus*, which cleaves the peptide bond at the carboxylic group of the Glu residue;

nonspecific enzymes, such as thermolysin originating from the bacterium *Bacillus thermoproteolyticus*, which hydrolyzes the peptide bond of the $NH_2$ group of hydrophobic amino acids (Xaa-Leu, Xaa-Ile, Xaa-Phe), and subtilisin and pronase which are bacterial proteases which hydrolyze practically all the bonds and can convert proteins into oligopeptides under controlled reaction conditions (enzyme concentration and reaction time).

Several proteases can be used simultaneously, if their modes of action are compatible, or they can be used successively. In the context of the invention, the digestion of the sample is preferably carried out via the action of a protease enzyme, for example trypsin.

Such a treatment step makes it possible to convert the large molecules represented by the proteins present in the sample into peptides, which are smaller molecules. The sensitivity of the detection subsequently obtained by mass spectrometry is thus increased. In addition, the treatment step makes it possible to generate several proteotypic peptides, also called reporter peptides, for a given target protein. The specificity of each proteotypic peptide must be verified by making sure, for example, that no other protein comprises an identical peptide sequence, or that no other transition interferes. The treatment thus makes it possible to increase the possibility of obtaining one or more proteotypic peptides specific for the protein to be assayed. Each proteotypic peptide makes it possible to quantify the protein by means of an independent assay. The specificity of MRM assays in complex fluids, such as blood samples, is not certain. Thus, in such a case, the assaying of several proteotypic peptides for each protein will make it possible to verify that each independent assay indeed results in the same dose. The obtaining of independent assays correctly correlated with one another will therefore make it possible to be sure of the specificity and of the robustness, in terms of reliability and reproducibility, of each assay taken individually.

Thus, in the rest of the method, each precursor ion having a given ratio $(m/z)_1$, which will be selected for the analysis by mass spectrometry, will result from a proteotypic peptide of the target protein to be assayed.

Depending on the complexity of the sample, the treatment step may be preceded by one or more optional steps. A very first step of fractionation of the proteins present in the sample of interest may be carried out in order to reduce the complexity of the sample, before the treatment of the remaining proteins. The term "fractionation" is intended to mean, conventionally, a purification of the number of proteins present: this can consist of the elimination of one or more proteins within the sample or a selection of one or more proteins, including the protein to be assayed. Such a step can consist of the depletion of the predominant proteins present in the sample, such as albumin, IgG, IgA, etc., these said proteins not corresponding to the protein of interest to be assayed. Such depletion can, for example, be carried out by affinity chromatography. This depletion makes it possible to reduce the complexity of the sample by reducing the number of proteins present. An albumin depletion has been proposed by the applicant (T. Fortin et al., above). The depletion of a larger panel of proteins has also been used by other teams (H. Keshishian et al., above and V. Kulasingam et al., above). These techniques may be implemented in the context of the invention. Nevertheless, affinity chromatography has the drawback of using an expensive chromatographic medium when it involves an immunoaffinity resin. Furthermore, if the specificity of the capture is insufficient, the protein to be assayed may itself also be partly retained by the affinity resin and lost for the subsequent assay, as demonstrated by T. Fortin et al., above.

Another alternative for fractionating the proteins consists in immunopurifying the protein of interest, for example by affinity chromatography. This method makes it possible to drastically reduce the complexity of the sample by obtaining a fraction comprising only the protein to be assayed (and possibly a few contaminating proteins). Such an approach is described by Kulasingam et al., above. Nevertheless, advantageously, the method according to the invention will not implement such a technique that requires having antibodies for the protein to be assayed. This is because the method according to the invention, by virtue of its specificity with respect to the protein to be assayed, makes superfluous a fractionation of the proteins resulting in a very small number of remaining proteins.

Another alternative for fractionating the proteins consists in purifying the sample to be assayed, by SDS-PAGE electrophoresis, and then in cutting out the band corresponding to the molecular mass of the protein to be assayed, as in particular described by S. A. Gerber et al., above. Generally, all the protein fractionation techniques of the electrophoresis, chromatography, etc., type, well known to those skilled in the art, can be used to reduce the complexity of the sample.

Another optional step of denaturation, reduction and then blocking of the thiol functions of the proteins may be carried out, in particular, before the treatment step leading to the cleavage of the proteins, and after the protein fractionation step, when the latter is present. This step, although optional, makes it possible to increase the digestion treatment yield and ensures better robustness of the subsequent assay. Owing to their three-dimensional conformation, certain proteins naturally withstand the proteolytic action of proteases (V. Brun et al., MCP, 2007, 2139-2149). In such a case, a step of denaturation, reduction and then blocking of the thiol functions of the proteins facilitates the action of the proteases and ensures a similar digestion treatment yield from one sample to another. All the proteins present in the sample of interest can be denatured and reduced, with, for example, urea or guanidine and dithiothreitol (DTT) or tris(2-carboxyethyl)phosphine (TCEP) (M. Sun et al., Bioconjug. Chem. 2005, 16(5): 1282-1290). The free thiol functions generated are then blocked with, for example, iodoacetamide or acrylamide (B. Herbert et al. Electrophoresis, 2001, 22: 2046-2057).

According to the method of the invention, at least one proteotypic peptide generated during the treatment step is assayed by mass spectrometry. Generally, a single proteotypic peptide per protein is assayed. It is nevertheless possible to assay several peptides per protein. It is also possible to successively assay proteotypic peptides from various proteins. All the peptides generated during the treatment step can be injected into the mass spectrometer. However, most commonly, the peptides generated will be fractionated, in particular in order to focus the assay on proteotypic peptides of the protein of interest. Such a fractionation of the peptides can, for example, be carried out by electrophoresis or chromatography techniques. These separative techniques can be used alone or combined with one another so as to obtain a multi-dimensional separation. For example, a multidimensional chromatography can be used by combining a separation by ion exchange chromatography with a reverse-phase chromatography, as described by T. Fortin et al., above and H. Keshishian et al., above. In these publications, the chromatographic medium can be in a column or in a cartridge (solid-phase extraction).

The electrophoretic or chromatographic fraction (or the retention time in one-dimensional or multidimensional chromatography) of the proteotypic peptides is characteristic of each peptide, and the implementation of these techniques therefore makes it possible to select the proteotypic peptide(s) to be assayed. Such a fractionation of the peptides generated makes it possible to increase the specificity of the subsequent assay by mass spectrometry.

An alternative to the electrophoresis or chromatography techniques, for fractionating the peptides, consists in specifically purifying the N-glycopeptides (J. Stal-Zeng et al., MCP, 2007, 1809-1817 and patent application WO 2008/066629). However, such purification only allows the quantification of peptides having undergone a post-translational modification of N-glycosylation type. As it happens, not all proteins are glycosilylated, which therefore limits its use.

Another alternative for fractionating the peptides consists in immunopurifying the peptide of interest, for example by affinity chromatography. This method makes it possible to drastically reduce the complexity of the sample by obtaining a fraction comprising only the peptide to be assayed (and possibly a few contaminating peptides). Such an approach, called SISCAPA, is described in L. Anderson et al., above, and in patent application US 2004/0072251. However, the obtaining of specific anti-peptide antibodies can be difficult and, in this case, the method according to the invention will not implement such a technique. Furthermore, the method according to the invention, by virtue of its specificity with respect to the protein to be assayed, makes superfluous an immunoaffinity fractionation of the peptides resulting in the single proteotypic peptide to be assayed.

In conclusion, in the context of the method according to the invention, the quantitative assaying of the generated peptides by mass spectrometry (corresponding to step b)) is preferably preceded by a chromatographic or electrophoretic separation of the peptides generated in step a). Such a chromatographic separation will preferably use a separation by reverse-phase chromatography, microflow chromatography, i.e. chromatography with a flow rate of from 100 µl to 500 µl per minute, or else purification by solid-phase extraction (SPE).

Step b) of the method according to the invention consists of the detection of at least one proteotypic peptide generated, during the preceding steps, by a mass spectrometry technique. Generally, a single proteotypic peptide is assayed per protein, but it could be possible to assay two or more thereof, the order of their arrival being conditioned upstream of the mass spectrometer, by the selected peptide fractionation technique.

Various mass spectrometer models can be used in the context of the invention. These models must allow three separation steps according to the m/z ratio with two successive fragmentations interspersed between the separation steps, i.e. a type of analysis called MS/MS/MS or alternatively $MS^3$. By way of example, mention may be made of the models of triple quadrupole type (L. Anderson & C. Hunter, MCP, 2006, 573-588 . . . ), or of ion trap type (B. Han & R. Higgs, Brief Funct Genomic Proteomic. 2008 September; 7(5): 340-54), or else of time-of-flight type (MALDI-TOF) (K.-Y. Wang et al., Anal Chem, 2008, 80(16) 6159-6167). Models of hybrid triple quadrupole type, integrating an ion trap, are nevertheless preferred. The peptides to be assayed, most commonly in solution, are injected and assayed in the mass spectrometer chosen.

In a first step i), the peptides resulting from the treatment of the proteins leading to their cleavage, which are injected into the mass spectrometer, are ionized to give molecular ions, called precursors given that they will subsequently be subjected to fragmentation in order to generate fragment ions. In order to be injected into the mass spectrometer, the peptides are generally dissolved in an aqueous solution. The sample to be assayed will therefore preferably be liquid. The ion source in which the molecules are ionized is, for example, of the MALDI (Matrix Assisted Laser Desorption Ionisation) or Electrospray (ESI from ElectroSpray Ionisation) type. Electrospray ionization, carried out under mild conditions, in particular at atmospheric pressure and ambient temperature, is nevertheless preferred.

The precursor ions generated are then filtered according to their mass m/z, and a precursor ion of given mass $(m/z)_1$ is selected according to the target protein sought. For this, conventionally, the ions are accelerated in an electric field, and then directed into an electric and/or magnetic field according to a trajectory which depends on their mass/charge (m/z) ratio. A variation in the electric and/or magnetic field applied makes it possible to vary the trajectory of the precursor ions, and thus makes it possible to select the $(m/z)_1$ ratio desired. According to a preferred characteristic of the invention, the precursor ion selected is a doubly-charged peptide which contains a number n of from 6 to 15 amino acids, and which has at least one proline in positions 2 to n–2 and/or one histidine in positions 1 to n—2. Such a selection will make it possible to obtain good specificity and selectivity in the subsequent steps with an improvement in the signal to noise ratio. According to one preferred embodiment, the selected precursor ion is doubly charged and has at least two prolines or one proline and one histidine. This is because the use of precursor ions having two prolines or one proline and one histidine generates even fewer secondary fragments in $MS^3$ and is even more suitable for obtaining the most effective quantitative assaying.

The expression "peptide comprising a proline (or a histidine) in positions 2 to n–2" is intended to mean that the latter can be in position 2, 3, 4, 5 . . . n–5, n–4, n–3 or n–2. Position 1 corresponds to the N-terminal part and position n to the C-terminal part, n corresponding to the number of amino acids present in the peptide.

The precursor ion selected, according to the target protein sought, is then fragmented into first-generation fragment ions in a step ii). The first-generation fragment ions generated are then filtered according to their mass m/z, and a given first-generation fragment ion having a mass $(m/z)_2$ is selected, in a step iii). According to an essential characteristic of the invention, the selected first-generation fragment ion corresponds to a double-charged peptide comprising a proline or a histidine in position 1 (N-terminal). Indeed, when the precursor ion comprises a proline or a histidine, there is a first-generation fragment ion which corresponds to a fragmentation of the peptide bond in the N-terminal position with respect to the proline or to the histidine, respectively. In step iv) of the method according to the invention, the selected first-generation fragment ion will undergo a further fragmentation, and the particular choice of the precursor ion and of the first-generation fragment ion results in a good fragmentation and in the obtaining of intense peaks. In the context of the invention, the precursor ions having a ratio $(nm/z)_1$ and the first-generation fragment ions having a ratio $(m/z)_2$ are chosen so as to be characteristic of the protein to be assayed and to result in assays that are as sensitive as possible, as specific as possible and as robust as possible in terms of reproducibility and reliability.

The two successive fragmentations will conventionally be carried out by collision with an inert gas, such as nitrogen or argon, within an electric field, or else solely by the application of a difference in potential, for example in a time-of-flight tube. The characteristic of the electric field condition the intensity and the nature of the fragmentation. Thus, the electric field applied in the presence of an inert gas, for example in a quadrupole, conditions the collision energy supplied to the ions. This collision energy will be optimized, by those skilled in the art, so as to increase the sensitivity of the transition to be assayed. By way of example, it is possible to vary the collision energy between 5 and 180 eV in q2 in an AB SCIEX QTRAP® 5500 mass spectrometer from the company Applied Biosystems (Foster City, United States of America). Similarly, the duration of the collision step and the excitation energy within, for example, an ion trap will be optimized, by those skilled in the art, so as to result in the most sensitive assay possible. By way of example, it is possible to vary this duration, called excitation time, between 0.010 and 50 ms and the excitation energy between 0 and 1 (arbitrary unit) in Q3 in an AB SCIEX QTRAP® 5500 mass spectrometer from the company Applied Biosystems.

Steps i) to iii) correspond to the steps conventionally used in an MRM assay. Such steps can be carried out in a triple quadrupole in particular. A triple quadrupole comprises two quadrupole analyzers (called Q1 and Q3) in series, separated by a collision cell (called q2) often consisting of a shorter quadrupole. Of course, it is necessary to implement the method according to the invention in a mass spectrometer having the ability to fragment the first-generation fragment ions into second-generation fragment ions. The fragmentation of a first-generation fragment ion into a second-generation fragment ion and the selection of the first-generation fragment ion, in the context of the invention, can for example be carried out in Q3 of a triple quadrupole comprising an ion trap. Hybrid triple quadrupoles which have an ion-trap capacity in the quadrupole Q3 may be used. Such instruments are sold by the company Applied Biosystems under the names 3200QTRAP®, 4000QTRAP® or AB SCIEX QTRAP® 5500. It is also possible to fragment a first-generation fragment ion in the $MS^3$ mode in any ion-trap analyzer. In this case, the precursor ion is selected in the ion trap, and then fragmented into first-generation fragment ions. A first-generation fragment ion is in turn selected and then fragmented into second-generation ions in the same ion-trap device. The second-generation ions are finally detected by expelling them sequentially out of the ion trap to the detector.

In the context of the invention, conventionally, the quadrupole analyzer (Q1) makes it possible to filter the precursor molecular ions resulting from the selected proteotypic peptide, according to their mass to charge ratio $(m/z)_1$. Only the peptides having the $(m/z)_1$ mass/charge ratio of the precursor ion sought are transmitted to the second quadrupole (q2). The q2 analyzer makes it possible to fragment the precursor ions having a mass/charge ratio $(m/z)_1$ into first-generation fragment ions. The fragmentation is generally obtained by collision of the precursor peptides with an inert gas, such as nitrogen or argon. The first-generation fragment ions are then transmitted to a third quadrupole (Q3) which filters the first-generation fragment ions according to a mass to charge ratio (m/z). Only a first-generation fragment ion having the mass/charge ratio $(m/z)_2$ of a fragment characteristic of the proteotypic peptide sought will undergo the final steps of the method according to the invention. Indeed, the method according to the invention comprises an additional fragmentation: in a subsequent step iv), the selected first-generation fragment ion having a mass $(m/z)_2$ is fragmented into second-generation fragment ions. After the selection in Q3 of a first-generation fragment ion having the mass/charge ratio $(m/z)_2$ of a fragment of the proteotypic peptide sought, this first-generation fragment ion is in turn fragmented, for example by virtue of an ion trap. Various second-generation fragment ions resulting from the fragmentation of the first-generation fragment ion are then obtained. These various second-generation ions will then be expelled to a detector, by the mass analyzer consisting, for example, of an ion trap or of a quadrupole. The expulsion is, for example, carried out sequentially out of the ion trap, by application of a voltage modulated as a function of time by a radiofrequency.

In order to detect the current induced, the second-generation fragment ions are directed to a detector which collects the second-generation fragment ions which arrive at different times according to the m/z ratio and which amplifies the signal associated with the ions. According to one variant of implementation of the method according to the invention, in step v), the intensity of the current induced by the second-generation fragment ions is detected as a function of time and the signal obtained over a given period is broken down into a mass spectrum of the various ions present according to their mass m/z, so as to obtain a mass peak associated with each of the second-generation ions detected present over the given period, and the signal corresponding to the current of at least one selected second-generation ion is recomposed, and the intensity of the corresponding current measured is the quantitative measurement selected in step vi). In general, the total signal is obtained by time fraction, or period t. The duration of the periods t depends on the scan speed of the mass analyzer and on the range of masses to be scanned; it is generally less than one second. The total signal obtained over each given period t is broken down into a mass spectrum of the various ions present according to their mass m/z, so as to obtain a mass peak associated with each of the second-generation ions detected over this period t. The second-generation ions are observed for several consecutive periods t, corresponding to the period T during which the proteotypic peptide is eluted. The period t during which the signal of the second-generation fragment ions created by the proteotypic peptide is at a maximum corresponds to the elution time, or retention time, of the proteotypic peptide. The elution time of the proteotypic peptide can be determined, for example, conventionally by MRM, using a solution of the purified proteotypic peptide or a solution of the purified target protein or a solution in which one or other is particularly abundant. The minimum duration of the period T is conventionally from 5 to 30 s. However, the duration of the period T is generally extended, so that the measurement of the signal is not affected by a microvariation in the elution time of the proteotypic peptide. The duration of the period T can thus be extended to reach the total time of the chromatographic separation. However, conventionally, the period T is generally fixed between one minute and five minutes, centered on the elution time of the proteotypic peptide. The signal corresponding to the current of at least one second-generation ion, specific for the proteotypic peptide resulting from the protein to be quantified, can be selected for each fraction of time t, during the period T. This signal can then be extracted from the total signal. The intensity of the current corresponding to the sum of the intensities measured at each instant t of the period T or a fraction of the period T will correspond to the quantitative measurement selected in step vi). Indeed, as is detailed in example 1, the signal corresponding to the current generated by the ions detected, as a function of time, can be broken down for each given period t (which is in fact a very short period) and added, for example, for the fraction most representative of the period T, so as to obtain a mass spectrum of the various ions present according to their mass m/z. A mass peak associated with each of the second-generation ions detected in step v) and present over the most representative fraction of the period T is thus obtained. It is then possible to select one or more second-generation ions having a given mass and to recompose the signal corresponding to the current of the ions selected. The sum of the intensities of the current induced by the fragment ions of each period t, occurring during the fraction most representative of the period T, is thus obtained by integration of the sum of the signals observed during the consecutive periods t of the most representative fraction of the period T corresponding to the elution of the proteotypic peptide. This sum corresponds, for example, to the quantitative measurement which will make it possible to determine the amount of proteotypic peptide present. The first and the last period t of the most representative fraction of the period T of which the signals are added may correspond to the first and the last period t for which the signal is greater than the background noise of the detector. The intensity of current thus measured may serve as a quantitative measurement for determining the amount of proteotypic peptide present, which is characterized by its expression in the International System of units (SI units) of $mol/m^3$ or $kg/m^3$ type, or by multiples or submultiples of these units, or by the usual derivatives of SI units, including multiples or submultiples thereof. By way of non-limiting example, units such as ng/ml or fmol/l are units characterizing a quantitative measurement. Preferably, in step vi), the quantitative measurement associated with the second-generation fragment ion having the most intense m/z peak is selected. It is also possible to add the quantitative measurements of various second-generation fragment ions. In this case, in step vi), the correlation is, for example, carried out on the basis of the sum of at least two quantitative measurements (in particular two or three), each being associated with the second-generation fragment ions having the most intense m/z peaks.

A data processing computer assembly makes it possible to convert the information received by the detector into a mass spectrum. The intensity of current induced by the selected second-generation fragment ions, measured in the detector, is proportional to the amount of second-generation fragment ions, which is itself proportional to the amount of first-generation fragment ions, which is itself proportional to the amount of precursor ions obtained by ionization of the selected proteotypic peptide, which is itself proportional to the amount of protein to be assayed. The amount of current measured, induced by the second-generation fragment ions, is therefore directly proportional to the amount of protein to be assayed. The selection of at least one quantitative measurement associated with a second-generation ion, and the correlation of this quantitative measurement to the amount of proteotypic peptide generated and to the amount of protein present in the sample, makes it possible to obtain quantitative assaying.

A calibration is necessary in order to be able to correlate the area of the peak measured, corresponding to the intensity of current induced by the second-generation fragment ion(s), to the amount of corresponding second-generation fragment ions, which may itself be correlated to the amount of corresponding first-generation fragment ions, which may itself be correlated to the amount of precursor ions, which may itself be correlated to the amount of the protein of interest. For this, the conventional calibrations used in MRM assays may be implemented, in the context of the invention. MRM assays are conventionally calibrated using external standards or, preferably, using internal standards as described by T. Fortin et al., above. The correlation between the quantitative measurement and the amount of proteotypic peptide, and subsequently of target protein, is obtained by calibrating the signal measured relative to a standard signal for which the amount to be assayed is known. The calibration can be carried out by means of a calibration curve, for example obtained by means of successive injections of standard proteotypic peptide at various concentrations (external calibration), or preferentially by internal calibration using a heavy peptide, as an internal standard, for example in accordance with the AQUA, QconCAT or PSAQ methods detailed hereinafter. The term "heavy peptide" is intended to mean a peptide corresponding to the proteotypic peptide, but in which one or more carbon 12 ($^{12}C$) atoms is (are) replaced with carbon 13 ($^{13}C$), and/or one or more nitrogen 14 ($^{14}C$) atoms is (are) replaced with nitrogen 15 ($^{15}N$).

The use of heavy peptides, as internal standards (AQUA), has also been proposed by S. A. Gerber et al., above and in patent application US 2004/0229283. The principle is to artificially synthesize proteotypic peptides with amino acids comprising isotopes that are heavier than the usual natural isotopes. Such amino acids are obtained, for example, by replacing some of the carbon 12 ($^{12}C$) atoms with carbon 13 ($^{13}C$), or by replacing some of the nitrogen 14 ($^{14}N$) atoms with nitrogen 15 ($^{15}N$). The artificial peptide (AQUA) thus synthesized has rigorously the same physicochemical properties as the natural peptide (with the exception of a higher mass). It is generally added, at a given concentration, to the sample upstream of the assaying by mass spectroscopy, for example between the treatment leading to the cleavage of the proteins of the sample of interest and the fractionation of the peptides obtained after the treatment step. As a result, the AQUA peptide is copurified with the natural peptide to be assayed, during the fractionation of the peptides. The two peptides are therefore injected simultaneously into the mass spectrometer, for the assay. They then undergo the same ionization yields in the source. The comparison of the areas of the peak of the natural peptide and the AQUA peptide, the concentration of which is known, makes it possible to calculate the concentration of the natural peptide and thus to work back to the concentration of the protein to be assayed. A variant of the AQUA technique has been proposed by J.-M. Pratt et al. (Nat. Protoc. 2006, 1:1029-1043) under the name QconCAT. This variant is also described in patent application WO 2006/128492. It consists in concatenating various AQUA peptides and in producing the artificial polypeptide in the form of a heavy recombinant protein. The recombinant protein is synthesized with amino acids comprising heavy isotopes. In this way, it is possible to obtain a standard for calibrating the simultaneous assaying of several proteins at a lower cost. The QconCAT standard is added from the beginning, upstream of the treatment leading to the cleavage of the proteins and before the steps of protein fractionation, denaturation, reduction and then blocking of the thiol functions of the proteins, if said steps are present. The QconCAT standard therefore undergoes the same treatment cycle leading to the cleavage of the proteins as the natural protein, which makes it possible to take into account the yield of the treatment step leading to the cleavage of the proteins. Indeed, the treatment, in particular by digestion, of the natural protein may not be complete. In this case, the use of an AQUA standard would result in the amount of natural protein being underestimated. For absolute assaying, it may therefore be important to take into account the yields from treatment leading to the cleavage of the proteins. However, V. Brun et al. (MCP, 2007, 2139-2149) have shown that, sometimes, the QconCAT standards do not exactly reproduce the yield from treatment, in particular by digestion, of the natural protein, doubtless because of a different three-dimensional conformation of the QconCAT protein.

V. Brun et al. above have therefore proposed using a method called PSAQ and described in patent application WO 2008/145763. In this case, the internal standard is a recombinant protein, having the same sequence as the natural protein but synthesized with heavy amino acids. The synthesis is carried out ex vivo with heavy amino acids. This standard has rigorously the same physicochemical properties as the natural protein (with the exception of a higher mass). It is added from the beginning, before the protein fractionation step, when said step is present. It is therefore copurified with the native protein, during the protein fractionation step. It exhibits the same yield from treatment, in particular by digestion, as the native protein. The heavy peptide obtained after cleavage is also copurified with the natural peptide, if a peptide fractionation step is carried out. The two peptides are therefore injected simultaneously into the mass spectrometer, so as to be assayed quantitatively. They then undergo the same ionization yields in the source. Comparison of the peak areas of the natural peptides and of the reference peptides in the PSAQ method makes it possible to calculate the concentration of the protein to be assayed while taking into account all of the steps of the assaying method.

All of these techniques, namely AQUA, QconCAT or PSAQ or any other calibration technique, used in assays by mass spectrometry and in particular in MRM or MS assays, may be implemented in order to perform the calibration, in the context of the invention.

The method according to the invention may therefore be implemented for the quantitative and qualitative assaying of protein, for in vitro diagnosis applications in particular. TABLE 1A below details a certain number of proteins that can be assayed by means of the method according to the invention, and also the proteotypic peptide selected.

TABLE 1A

| Protein | Mass m/z of the precursor ion M2H+ | Mass of the proteotypic peptide | Position of the proteotypic peptide within the protein | Sequence of the proteotypic peptide |
|---|---|---|---|---|
| Plastin-1 | 730.37935 | 1458.7587 | 349-362 | SEQ ID No 8: QFVTPADVVSGNPK |
| Plastin-1 | 538.29145 | 1074.5829 | 42-51 | SEQ ID No 9: EASLPLPGYK |
| Plastin-1 | 535.81255 | 1069.6251 | 266-274 | SEQ ID No 10: LSPEELLLR |
| Ezrin | 553.2918 | 1104.5836 | 237-245 | SEQ ID No 11: IGFPWSEIR |
| Aminoacylase 1 | 446.2309 | 890.4618 | 277-284 | SEQ ID No 12: VAPDVDFK |
| Fatty acid-binding protein (L-FABP) | 606.35205 | 1210.7041 | 21-31 | SEQ ID No 13: AIGLPEELIQK |
| Protein disulfide isomerase | 983.522 | 1965.044 | 231-247 | SEQ ID No 14: HNQLPLVIEFTEQTAPK |
| Protein disulfide isomerase | 761.87715 | 1521.7543 | 18-30 | SEQ ID No 15: DAPEEEDHVLVLR |
| Protein disulfide isomerase | 726.8506 | 1451.7012 | 327-338 | SEQ ID No 16: YKPESEELTAER |
| Protein disulfide isomerase | 541.8384 | 1081.6768 | 255-263 | SEQ ID No 17: THILLFLPK |
| Protein disulfide isomerase | 486.2678 | 970.5356 | 402-409 | SEQ ID No 18: QLAPIWDK |
| Protein disulfide isomerase | 465.2625 | 928.525 | 437-444 | SEQ ID No 19: VHSFPTLK |
| Protein disulfide isomerase | 456.22085 | 910.4417 | 445-452 | SEQ ID No 20: FFPASADR |
| Protein disulfide isomerase | 432.23345 | 862.4669 | 58-65 | SEQ ID No 21: ALAPEYAK |
| Protein disulfide isomerase | 431.1965 | 803.3716 | 310-316 | SEQ ID No 22: EECPAVR |
| Keratin, type 1 cytoskeletal 20 | 932.482 | 1846.9691 | Nov. 28 | SEQ ID No 23: SLSSSLQAPVVSTVGMQR |

TABLE 1A-continued

| Protein | Mass m/z of the precursor ion M2H+ | Mass of the proteotypic peptide | Position of the proteotypic peptide within the protein | Sequence of the proteotypic peptide |
|---|---|---|---|---|
| Keratin, type 1 cytoskeletal 20 | 658.8188 | 1315.6376 | 308-318 | SEQ ID No 24: ESLEHTLEETK |
| Keratin, type 1 cytoskeletal 20 | 647.32965 | 1292.6593 | 29-42 | SEQ ID No 25: LGTTPSVYGGAGGR |
| Keratin, type 1 cytoskeletal 20 | 583.2716 | 1164.5432 | 104-112 | SEQ ID No 26: QWYETNAPR |
| Keratin, type 1 cytoskeletal 20 | 544.7891 | 1087.5782 | 179-187 | SEQ ID No 27: VFDDLTLHK |
| 14-3-3 sigma protein | 528.2675 | 1054.535 | 161-169 | SEQ ID No 28: EMPPTNPIR |
| S100-A11 protein Calgizarin | 510.7502 | 1019.5004 | 04 Dec. | SEQ ID No 29: ISSPTETER |
| S100-A11 protein Calgizarin | 386.69975 | 771.3995 | 56-62 | SEQ ID No 30: DPGVLDR |

The proteins studied correspond to the following number in the Swiss Prot database: Plastin-1 (Q14651), Ezrin (P15311), Aminoacylase 1 (Q03154), Protein disulfide isomerase (P07237), keratin, type 1 cytoskeletal 20 (P35900), 14-3-3 sigma protein (P31947), S100-A11 protein Calgizarin (P31949).

The theoretical mass of the proteotypic peptide is determined from its amino acid sequence. Many software packages make it possible to perform this calculation, such as MRM Pilot (Applied Biosystems), Sequence Editor (Bruker Daltonik, Bremen, Germany), etc. The calculation given in TABLE 1A was performed with MRM Pilot. The theoretical mass of the doubly-charged precursor ion (M2H$^+$) is determined by adding the mass of two protons to the theoretical mass of the proteotypic peptide, and dividing the sum obtained by 2.

TABLE 1B gives, for each protein, according to the doubly-charged precursor ion selected, the position of the prolines and histidines present and the number of amino acids present (AA meaning amino acid).

TABLE 1B

| Protein | Sequence of the proteotypic peptide | Position 1$^{st}$ proline | Position 2$^{nd}$ proline | Number AA between 1$^{st}$ proline and C-term | Position 1$^{st}$ His | Number AA between 1$^{st}$ His and C-term | Total number AA |
|---|---|---|---|---|---|---|---|
| Plastin-1 | SEQ ID No 8 | 5 | 13 | 9 | — | — | 14 |
| Plastin-1 | SEQ ID No 9 | 5 | 7 | 5 | — | — | 10 |
| Plastin-1 | SEQ ID No 10 | 3 | — | 6 | — | — | 9 |
| Ezrin | I SEQ ID No 11 | 4 | — | 5 | — | — | 9 |
| Aminoacylase 1 | SEQ ID No 12 | 3 | — | 5 | — | — | 8 |
| Fatty acid-binding protein (L-FABP) | SEQ ID No 13 | 5 | — | 6 | — | — | 11 |
| Protein disulfide isomerase | SEQ ID No 14 | 5 | 16 | 12 | 1 | 16 | 17 |
| Protein disulfide isomerase PDI A1 | SEQ ID No 15 | 3 | — | 10 | 8 | 5 | 13 |
| Protein disulfide isomerase | SEQ ID No 16 | 3 | — | 9 | — | — | 12 |
| Protein disulfide isomerase | SEQ ID No 17 | 8 | — | 1 | 2 | 7 | 9 |
| Protein disulfide isomerase | SEQ ID No 18 | 4 | — | 4 | — | — | 8 |
| Protein disulfide isomerase | SEQ ID No 19 | 5 | — | 3 | 2 | 6 | 8 |
| Protein disulfide isomerase | SEQ ID No 20 | 3 | — | 5 | — | — | 8 |

TABLE 1B-continued

| Protein | Sequence of the proteo-typic peptide | Position 1st proline | Position 2nd proline | Number AA between 1st proline and C-term | Position 1st His | Number AA between 1st His and C-term | Total number AA |
|---|---|---|---|---|---|---|---|
| Protein disulfide isomerase | SEQ ID No 21 | 4 | — | 4 | — | — | 8 |
| Protein disulfide isomerase | SEQ ID No 22 | 4 | — | 3 | — | — | 7 |
| Keratin, type 1 cytoskeletal 20 | SEQ ID No 23 | 9 | — | 9 | — | — | 18 |
| Keratin, type 1 cytoskeletal 20 | SEQ ID No 24 | — | — | — | 5 | 6 | 11 |
| Keratin, type 1 cytoskeletal 20 | SEQ ID No 25 | 5 | — | 9 | — | — | 14 |
| Keratin, type 1 cytoskeletal 20 | SEQ ID No 26 | 8 | — | 1 | — | — | 9 |
| Keratin, type 1 cytoskeletal 20 | SEQ ID No 27 | — | — | — | 8 | 1 | 9 |
| 14,3,3 sigma protein | SEQ ID No 28 | 3 | 4 | 6 | — | — | 9 |
| S100-A11 protein Calgizarin | SEQ ID No 29 | 4 | — | 5 | — | — | 9 |
| S100-A11 protein Calgizarin | SEQ ID No 30 | 2 | — | 5 | — | — | 7 |

Only the proteotypic peptide HNQLPLVIEFTEQTAPK (SEQ ID No 14) comprising 17 amino acids, in the case of the protein disulfide isomerase protein, and the peptide SLSSS-LQAPWSTVGMQR (SEQ ID No 23) comprising 18 amino acids, in the case of the keratin, type 1 cytoskeletal 20 protein, do not result in any detection of the corresponding doubly-charged precursor ion. TABLE 1C gives, for each protein, the doubly-charged 1st-generation fragment ion selected, with the position of the prolines and histidines present.

TABLE 1C

| Protein | Sequence of the proteotypic peptide | Doubly-charged first-generation fragment | Position of the first proline | Position of the first histidine |
|---|---|---|---|---|
| Plastin-1 | SEQ ID No 8 | SEQ ID No 31: PADVVSGNPK | 1 | — |
| Plastin-1 | SEQ ID No 9 | SEQ ID No 32: PLPGYK | 1 | — |
| Plastin-1 | SEQ ID No 10 | SEQ ID No 33: PEELLLR | 1 | — |
| Ezrin | SEQ ID No 11 | SEQ ID No 34: PWSEIR | 1 | — |
| Aminoacylase 1 | SEQ ID No 12 | SEQ ID No 35: PDVDFK | 1 | — |
| Fatty acid-binding protein (L-FABP) | SEQ ID No 13 | SEQ ID No 36: PEELIQK | 1 | — |
| Protein disulfide isomerase | SEQ ID No 14 | — | — | — |
| Protein disulfide isomerase | SEQ ID No 15 | SEQ ID No 37: PEEEDHVLVLR | 1 | 6 |
| Protein disulfide isomerase | SEQ ID No 16 | SEQ ID No 38: PESEELTAER | 1 | — |
| Protein disulfide isomerase | SEQ ID No 17 | SEQ ID No 39: HILLFLPK | 7 | 1 |
| Protein disulfide isomerase | SEQ ID No 18 | SEQ ID No 40: PIWDK | 1 | — |
| Protein disulfide isomerase | SEQ ID No 19 | SEQ ID No 41: HSFPTLK | 4 | 1 |

TABLE 1C-continued

| | Sequence of the proteotypic peptide | Doubly-charged first-generation fragment | Position of the first proline | Position of the first histidine |
|---|---|---|---|---|
| Protein disulfide isomerase | SEQ ID No 20 | SEQ ID No 42: PASADR | 1 | — |
| Protein disulfide isomerase | SEQ ID No 21 | SEQ ID No 43: PEYAK | 1 | — |
| Protein disulfide isomerase | SEQ ID No 22 | SEQ ID No 44: PAVR | 1 | — |
| Keratin, type 1 cytoskeletal 20 | SEQ ID No 23 | — | — | — |
| Keratin, type 1 cytoskeletal 20 | SEQ ID No 24 | SEQ ID No 45: HTLEETK | 1 | — |
| Keratin, type 1 cytoskeletal 20 | SEQ ID No 25 | SEQ ID No 46: PSVYGGAGGR | 1 | — |
| Keratin, type 1 cytoskeletal 20 | SEQ ID No 26 | — | — | — |
| Keratin, type 1 cytoskeletal 20 | SEQ ID No 27 | — | — | — |
| 14-3-3 sigma protein | SEQ ID No 28 | SEQ ID No 47: PPTNPIR | 1 | — |
| S100-A11 protein Calgizarin | SEQ ID No 29 | SEQ ID No 48: PTETER | 1 | — |
| S100-A11 protein Calgizarin | SEQ ID No 30 | SEQ ID No 49: PGVLDR | 1 | — |

The examples hereinafter, with reference to the appended figures, are in no way limiting in nature and make it possible to illustrate the invention.

Figure 6A:
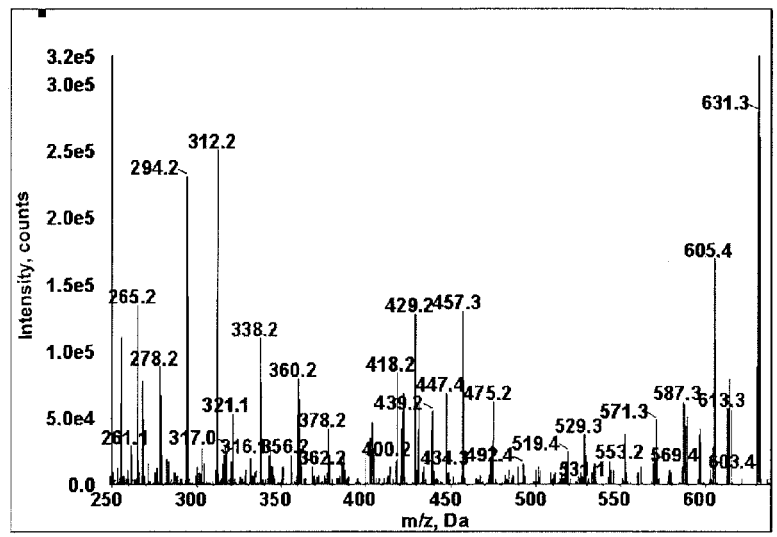
Figure 6B:
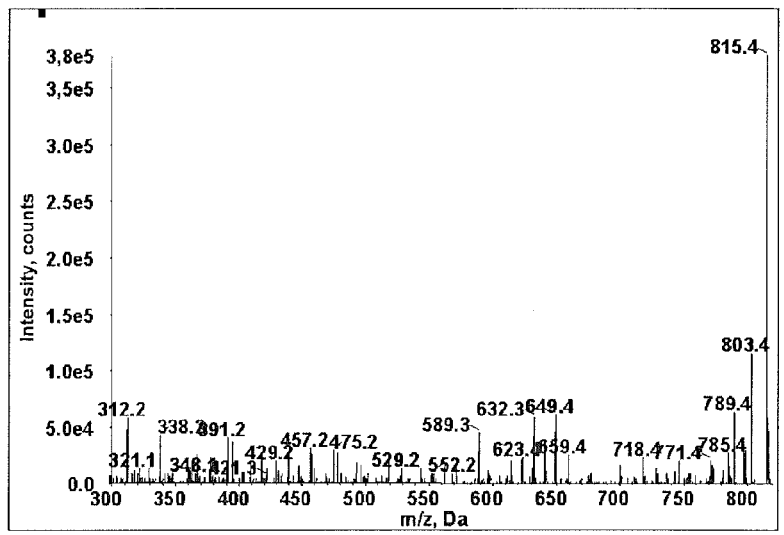
Figure 6C:
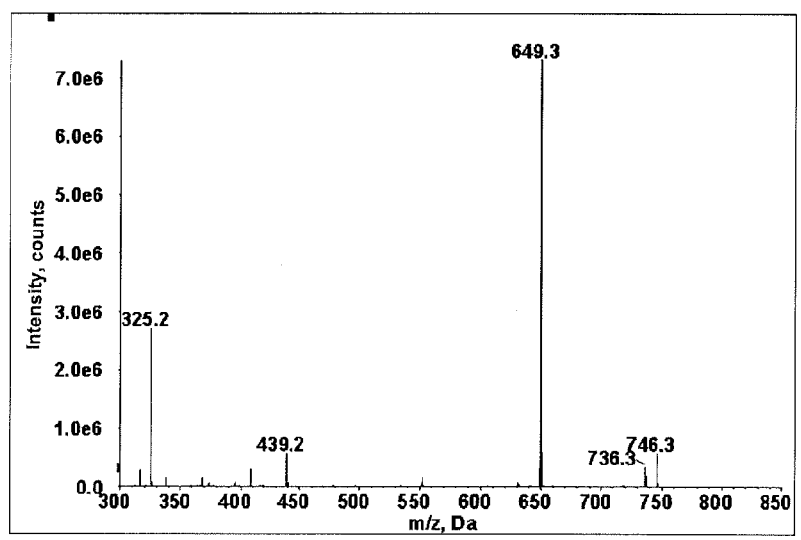

FIGS. 6A, 6B and 6C represent the mass spectra of the second-generation fragment ions obtained from the proteotypic peptide SAPSPLTYR (SEQ ID No 53) of the Tp435 protein when choosing, as first-generation fragment ion, either the most intense singularly-charged fragment ion (FIG. 6A—elution between 0.098 and 0.300 min), or the fragment ion containing a proline in singularly-charged form (FIG. 6B—elution between 0.101 and 0.306 min), or this same ion in double-charged form (FIG. 6C—elution between 0.102 and 0.298 min).

EXAMPLE 1

Principle of Quantitative Assaying by MRM$^3$ with External Calibration of a Tumor Marker: Prostate Specific Antigen (PSA)

PSA (prostate specific antigen, supplied by the British company Scipac) is used at the concentrations described below in female serum (Etablissement Français du Sang [French Blood Bank]) so as to form the points of the calibration range:

35 µl of PSA at 1.14 mg/ml in 165 µl of female serum so as to obtain a point at 200 µg/ml 50 µl of the point at 200 µg/ml in 150 µl of female serum so as to obtain a point at 50 µg/ml 40 µl of the point at 50 µg/ml in 160 µl of female serum so as to obtain a point at 10 µg/ml 20 µl of the point at 10 µg/ml in 180 µl of H$_2$O so as to have a point at 1 µg/ml 20 µl of the point at 1 µg/ml in 180 µl of H$_2$O so as to have a point at 100 ng/ml 20 µl of the point at 100 ng/ml in 180 µl of H$_2$O so as to have a point at 10 ng/ml 20 µl of the point at 10 ng/ml in 180 µl of H$_2$O so as to have a point at 1 ng/ml 20 µl of the point at 50 µg/ml in 180 µl of H$_2$O so as to have a point at 5 µg/ml 20 µl of the point at 5 µg/ml in 180 µl of H$_2$O so as to have a point at 500 ng/ml 20 µl of the point at 500 ng/ml in 180 µl of H$_2$O so as to have a point at 50 ng/ml.

200 µl of female serum are used to obtain a point at 0 ng/ml.

The range points and the serum samples to be assayed, which are samples taken from patients suffering from prostate cancer or from benign prostatic hyperplasia, are then digested according to the following protocol:
- Dilution of a volume of 100 µl of serum in 3 ml of 50 mM bicarbonate, pH=8.0.
- Addition of dithiothreitol (DTT) so as to obtain a final concentration of 15 mM.
- Reduction at 60° C. for 40 minutes.
- Cooling of the tubes to ambient temperature.
- Addition of iodoacetamide so as to obtain a final concentration of 25 mM.
- Alkylation for 40 minutes at ambient temperature and in the dark.
- Addition of trypsin with a ratio of 1/30.
- Digestion at 37° C. for 4 hours.
- Addition of DTT so as to obtain a final concentration of 10 mM.
- Reduction at 60° C. for 40 minutes.
- Cooling of the tubes at ambient temperature.
- Addition of iodoacetamide so as to obtain a final concentration of 15 mM and to allow alkylation of the thiol functions at ambient temperature and in the dark for 40 minutes.
- Addition of trypsin with a mass ratio of 1/30.
- Digestion at 37° C. overnight.

The serum is then desalted and concentrated according to the following protocol:
- Acidification of the samples with formic acid (i.e. 0.1% final concentration).
- Equilibration of Waters HLB Oasis columns with 1 ml of methanol and then 1 ml $H_2O$/0.1% formic acid.
- Loading of the sample, which flows by gravity.
- Washing with 1 ml $H_2O$/0.1% formic acid.
- Elution with 1 ml of 80% methanol in an $H_2O$/0.1% formic acid mixture.

The fraction eluted is then diluted in 3 ml of 200 mM ammonium acetate buffer at pH 3.00.

The sample is fractionated on a Waters Oasis MCX SPE cartridge according to the following protocol:
- The cartridge is conditioned with 1 ml of methanol and then 1 ml of 200 mM ammonium acetate buffer at pH 3.00.
- All of the serum diluted in the 200 mM ammonium acetate buffer at pH 3.00 is loaded onto the MCX cartridge, and then allowed to flow by gravity.
- The cartridge is washed with 1 ml of 200 mM ammonium acetate buffer at pH 3.00, and then with 1 ml of 80% methanol, 20% acetate buffer, pH 3.00.
- The elution is carried out with 1 ml of a 200 mM ammonium acetate buffer, pH 5.5/methanol (50/50).
- The eluate is evaporated with a SpeedVac® SPD2010-type evaporator (Thermo Electron Corporation, Waltham, Mass., United States of America), for 2 hours, in order to obtain a volume of approximately 100 µl.
- The eluate is then taken up in a mixture of 10% acetonitrile (ACN)/90% $H_2O$ 0.5% formic acid, quantity sufficient for (QS) 200 µl.

A volume of 100 µl of the sample obtained is injected and analyzed according to the following conditions:
- Ultimate 3000 chromatographic system from the company Dionex (Sunnyvale, Calif., United States of America)
- Waters Symmetry C18 column, 2.1 mm internal diameter, 100 mm long, particle size 3.5 µm
- Solvent A: $H_2O$+0.1% formic acid
- Solvent B: ACN+0.1% formic acid HPLC gradient defined in TABLE 2 hereinafter:

TABLE 2

| Time | Flow rate (µl) | Solvent A (%) | Solvent B (%) |
|---|---|---|---|
| 0 | 300 | 95 | 5 |
| 3 | 300 | 95 | 5 |
| 15 | 300 | 78 | 22 |
| 16 | 300 | 0 | 100 |
| 24 | 300 | 0 | 100 |
| 24.1 | 300 | 95 | 5 |
| 32 | 300 | 95 | 5 |

The eluate leaving the chromatographic column is directly injected into the ionization source of the QTRAP® 5500 mass spectrometer from the company Applied Biosystems (Foster City, United States of America).

The machine parameters used are the following:
- Scan type: MS/MS/MS (MS3)
- Polarity: Positive
- Scan mode: Profile
- Ionization source: Turbo V™ (Applied BioSystems)
- Precursor: 636.80 Da
- $1^{st}$ generation ion: 472.30 Da
- Q1 setting: Filtering with unit resolution
- Q3 setting: Linear ion trap
- Scan speed: 10000 Da/s
- Trapping in Q0: Yes
- Linear ion trap fill time in Q3: 200.00 ms
- Q3 input voltage: 8.00 V
- Fragmentation: Yes
- Excitation time: 25.00 ms
- Ion trap scan increment in Q3: 0.12 Da
- Mass at start of scan (Da): 500.00 Da
- Mass at end of scan (Da): 850.00 Da
- Time (s): 0.0350 s
- Trapping radiofrequency amplitude, start: 4.30
- Trapping radiofrequency amplitude, end: 4.48
- Ion trap output voltage (start): −136.24 V
- Ion trap output voltage (end): −125.09 V
- Curtain gas: 50.00 psi
- Cone voltage: 5500.00 V
- Source temperature: 500.00° C.
- Nebulizing gas: 50.00 psi
- Heating gas: 40.00 psi
- Collision cell filling: High
- Declustering potential: 50.00 V
- Input potential before Q0: 3.00 V
- Collision energy: 28.00 eV
- Excitation energy (AF2): 0.07

Figure 1A:
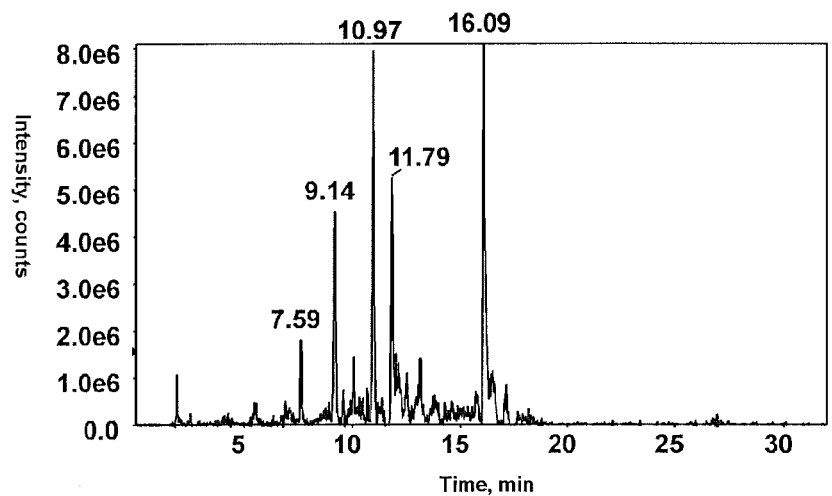
FIG. 1A shows an example of signal obtained, as a function of time, in the form of a total ion chromatogram.

The signal obtained is represented as a function of time in the form of a total ion chromatogram (FIG. 1A).

Figure 1B:
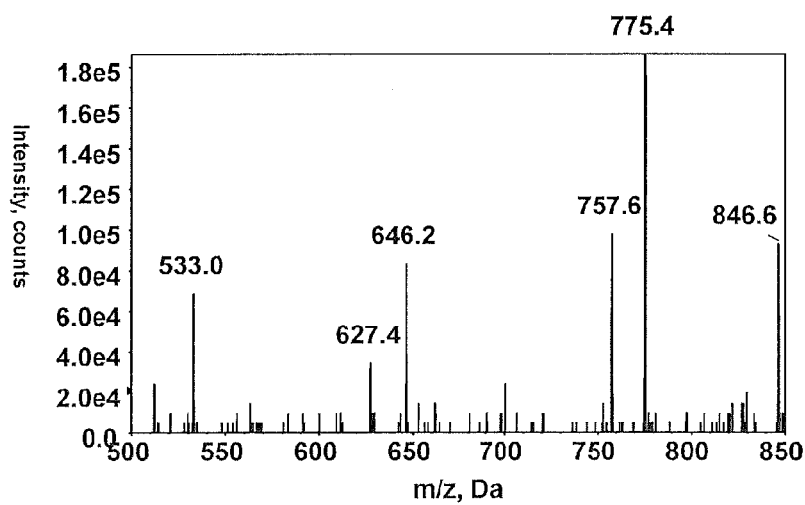
FIG. 1B represents the mass spectrum of the second-generation fragment ions eluted between 11.70 and 11.90 minutes in FIG. 1A.

At each instant t, the second-generation ion masses can be observed in the form of a mass spectrum. A mass spectrum therefore measures the masses of the various entities eluted from the column and simultaneously injected into the mass spectrometer. Thus, the second-generation fragment ion masses eluted between 11.70 and 11.90 minutes are shown in FIG. 1B. Some of these masses correspond to the masses of second-generation fragments of the proteotypic peptide LSEPAELTDAVK (SEQ ID No 50) of PSA. Thus, the masses 533.0, 646.2, 757.6, 775.4 and 846.6 correspond, respectively, to the fragments y5, y6, y7-$H_2O$, y7 and y8. As is well known in the prior art, by convention, the "y5" fragment is a fragment of which the sequence is the last 5 amino acids of the sequence of the proteotypic peptide, the "y6" fragment the last six, etc.

Figure 1C:
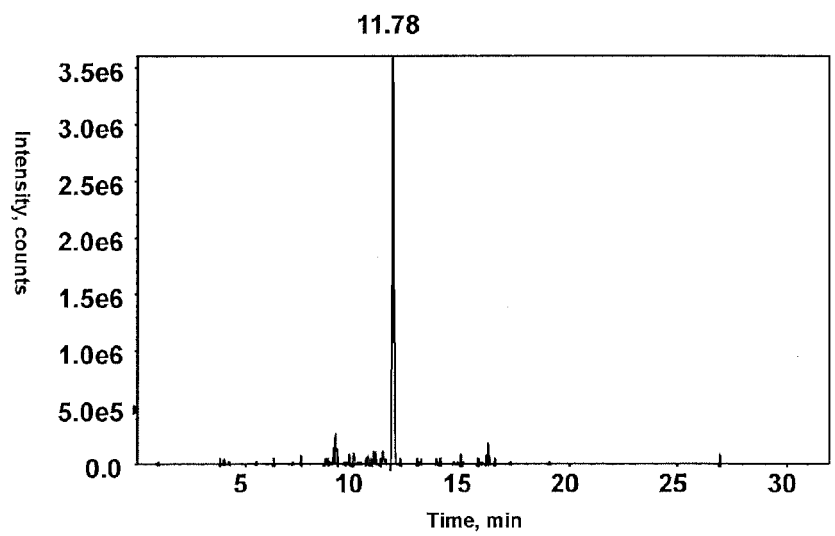
FIG. 1C shows the sum of the chromatograms of the extracted ions corresponding to the masses of the second-generation fragments y5, y6, y7-H$_2$O, y7 and y8 of the proteotypic peptide LSEPAELTDAVK (SEQ ID No 50) of PSA, smoothed over three points, of FIG. 1A.

The Analyst 1.5 software (Applied Biosystems) makes it possible to extract the ion current corresponding to windows of mass as a function of time. It therefore makes it possible to obtain a chromatogram for windows, for example of a unit of mass, corresponding to each second-generation fragment of interest. This chromatogram is called an extracted ion chromatogram. The Analyst 1.5 software also makes it possible to add together several extracted ion chromatograms. It also makes it possible to carry out smoothing of the signal according to the Stavitzky and Golay algorithm (A. Savitzky and M. Golay (1964). *Smoothing and Differentiation of Data by Simplified Least Squares Procedures*. Analytical Chemistry, 36: 1627-1639). Thus, FIG. 1C shows the sum of the extracted ion chromatograms corresponding to the masses of the second-generation fragments y5, y6, y7-$H_2O$, y7 and y8 of the proteotypic peptide LSEPAELTDAVK (SEQ ID No 50) of PSA, smoothed over three points.

The Analyst 1.5 software then makes it possible to integrate the area under the peaks observed on the extracted ion chromatograms. Thus, the measurement of the signal of the sum of the y5, y6, y7-$H_2O$, y7 and y8 ions of the peptide LSEPAELTDAVK (SEQ ID No 50), for the points of ranges having an amount of PSA of between 0 and 1000 ng/ml, made it possible to obtain TABLE 3 hereinafter:

TABLE 3

| Area under the peaks | PSA concentration (ng/ml) |
| --- | --- |
| 1.25e+005 | 0 |
| 4.99e+005 | 1 |
| 1.50e+006 | 5 |
| 1.62e+006 | 10 |
| 9.42e+006 | 50 |
| 1.90e+007 | 100 |
| 9.73e+007 | 500 |
| 1.90e+008 | 1000 |

Figure 1D:
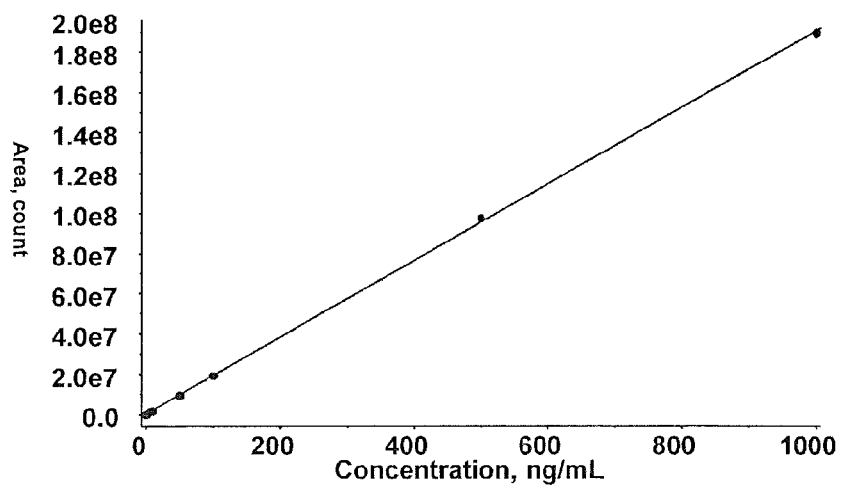
FIG. 1D is an example of a calibration curve.

These results make it possible to establish the calibration curve represented in FIG. 1D. This curve is modeled using a linear regression in the form of an equation ($y=1.9\times10^5 X + 2.76\times10^5$) which makes it possible to calculate the PSA concentration for any human serum sample having an unknown amount of PSA.

By way of example, the following patients' sera are assayed and make it possible to obtain the following amounts given in TABLE 4:

TABLE 4

| Patients | Area under the peak | Calculated concentration (ng/ml) |
| --- | --- | --- |
| B2004 | 1.81E+06 | 8.07 |
| D4003 | 8.48E+05 | 3.01 |
| D4004 | 1.37E+06 | 5.77 |

EXAMPLE 2

Principle of Quantitative Assaying by MRM[3] with Internal Calibration of a Tumor Marker: Prostate Specific Antigen (PSA)

An internal calibration standard is synthesized using amino acids comprising heavy isotopes for certain atoms, according to the protocol described in T. Tortin et al. (MCP, 2008 E-pub).

Thus, the organotypic peptide of PSA, LSEPAELTDAVK (SEQ ID No 50), is chemically synthesized with 2 alanines, each comprising 3 carbon 13 ($^{13}C$) atoms in place of the carbon 12 ($^{12}C$) atoms. The synthesis is carried out with an ABI433A synthesizer (Applied Biosystems, Foster City, United States of America) and L-($^{13}C_3$)alanine-N-FMOC (Euriso-Top, Saint-Aubin, France). At the end of synthesis, the heavy peptide is divided up into thirty 4-ml brown glass bottles, and then lyophilized.

The purity of the synthetic heavy peptide is verified by chromatography coupled to a mass analyzer (LCQ ion trap, ThermoFisher Scientific, Waltham, Mass., United States of America). It is established as greater than 95%. The amount of heavy peptide contained in the brown glass bottles is then established, on the basis of a sample of 3 bottles, with a model 1100 amino acid analyzer from the company Agilent Technologies (Massy, France). It is thus determined that the bottles contain 790 μg of more than 95% pure heavy peptide.

A bottle of 790 μg of heavy peptide is taken up with 1 ml of water to which 0.5% formic acid has been added. A stock solution of heavy peptide at a concentration of $6.2\times10^{-10}$ mol/μl is obtained.

The stock solution of the heavy peptide is diluted 10-fold in a mixture of acetonitrile/water (50/50) plus 1% formic acid in order to obtain a solution at $6.2\times10^{-11}$ mol/μl.

The solution at $6.2\times10^{-11}$ mol/μl is diluted 10-fold in a mixture of acetonitrile/water (50/50) plus 1% formic acid in order to obtain a solution at $6.2\times10^{-12}$ mol/μl.

The solution at $6.2\times10^{-12}$ mol/μl is diluted 20-fold in a mixture of acetonitrile/water (50/50) plus 1% formic acid in order to obtain a solution at $3.1\times10^{-13}$ mol/μl.

The solution at $3.1\times10^{-13}$ mol/μl is diluted 10-fold in a mixture of acetonitrile/water (50/50) plus 1% formic acid in order to obtain a solution at $3.1\times10^{-14}$ mol/μl.

The solution at $3.1\times10^{-14}$ mmol/μl is diluted 10-fold in a mixture of acetonitrile/water (50/50) plus 1% formic acid in order to obtain a solution at $3.1\times10^{-15}$ mol/μl.

The patient serum samples and the range points are treated according to the protocol described in example 1, with the addition of a volume of 50 μl of the heavy peptide solution at $3.1\times10^{-15}$ mol/μl between the enzymatic digestion step and the step of desalification on a Waters Oasis HLB column.

The patient serum samples and the range points are then analyzed according to the protocol described in example 1, with the addition of the monitoring of the ions corresponding to the heavy peptide, namely:

Precursor: 639.80 Da

1$^{st}$-generation ion: 475.30 Da

Figure 2A:
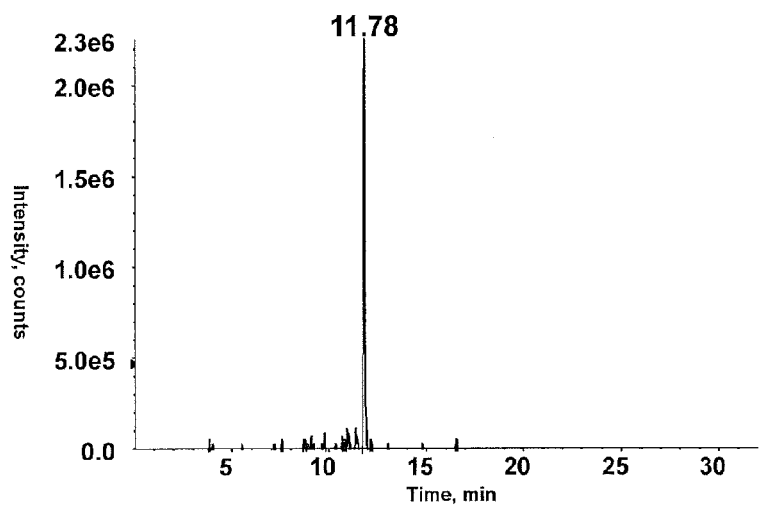
FIG. 2A represents the chromatogram obtained for the native peptide LSEPAELTDAVK (SEQ ID No 50) (retention time 11.78 min)
Figure 2B:
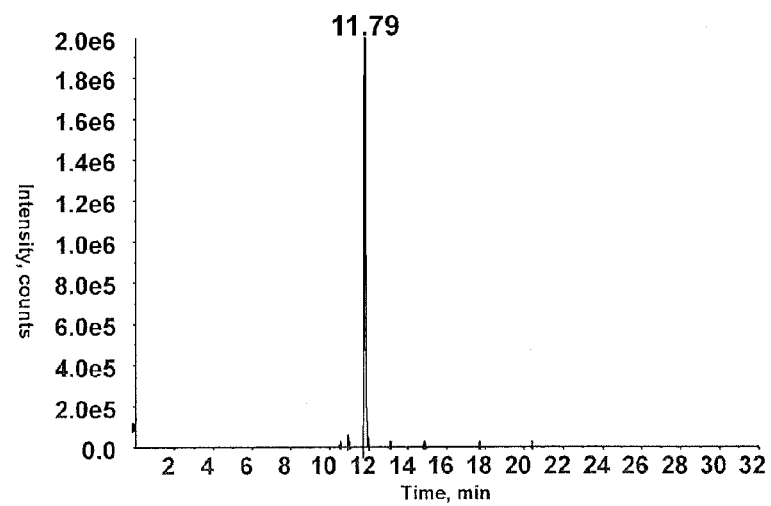
FIG. 2B represents that of the heavy peptide LSEPAELTDAVK (SEQ ID No 50) (retention time 11.79 min).

The heavy peptide LSEPAELTDAVK (SEQ ID No 50) has the same physicochemical properties as the native peptide, and consequently the same retention time in chromatography. The two peptides are therefore injected simultaneously into the mass spectrometer. This is what it is possible to observe on the chromatogram of the native peptide LSEPAELTDAVK (SEQ ID No 50) FIG. 2A (retention time 11.78 min) and of the heavy peptide LSEPAELTDAVK (SEQ ID No 50) FIG. 2B (retention time 11.79 min).

On the other hand, this heavy peptide comprises 6 mass units more than the native PSA peptide. It has a mass of 1271.66 g/mol compared with 1277.66 g/mol for the native peptide.

The amount of heavy peptide is known ($1.55\times10^{-13}$ mol) and is identical at all the points of the range; the reconstituted signal should therefore be constant throughout the range. However, a variation in the signal can be observed on the heavy peptide, which means that this same variation has impacted the signal of the native peptide. It is therefore possible to use the signal of the heavy peptide to correct the signal of the light peptide. To do this, a ratio between the areas of the chromatographic peaks of the specific second-generation native and heavy ions that have been extracted and added together is determined with the Analyst 1.5 software.

Thus, the measurement of the signals of the sums of the y5, y6, y7-H$_2$O, y7 and y8 ions of the native and heavy peptides LSEPAELTDAVK (SEQ ID No 50), for the points of ranges having an amount of PSA of between 0 and 1000 ng/ml, makes it possible to obtain TABLE 5 hereinafter:

TABLE 5

| PSA concentration (ng/ml) | Area under the peak of the native peptide | Area under the peak of the heavy peptide |
| --- | --- | --- |
| 0 | 1.25E+05 | 8.11E+06 |
| 1 | 4.99E+05 | 9.42E+06 |
| 5 | 1.50E+06 | 8.96E+06 |
| 10 | 1.62E+06 | 9.11E+06 |
| 50 | 9.42E+06 | 9.80E+06 |
| 100 | 1.90E+07 | 7.48E+06 |
| 500 | 9.73E+07 | 8.89E+06 |
| 1000 | 1.90E+08 | 9.55E+06 |

Figure 3:
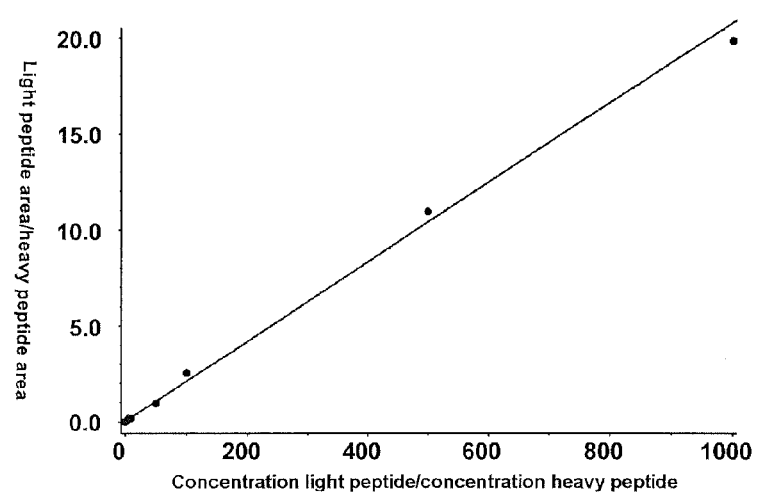
FIGS. 3, 4A and 4B are other examples of a calibration curve.

These results make it possible to establish the calibration curve represented in FIG. 3. This curve is modeled using a linear regression in the form of an equation (y=0.0208(Xnative/Xheavy)+0.0154) which makes it possible to calculate the PSA concentration for any human serum sample having an unknown amount of PSA.

By way of example, the following patients' sera are assayed and give the amounts shown in TABLE 6:

TABLE 6

| patients | Area under the peak of the native peptide | Area under the peak of the heavy peptide | Calculated concentration (ng/ml) |
| --- | --- | --- | --- |
| B2004 | 1.81E+06 | 8.74E+06 | 9.24 |
| D4003 | 8.48E+05 | 9.42E+06 | 3.6 |
| D4004 | 1.37E+06 | 8.26E+06 | 7.27 |

EXAMPLE 3

Comparison of the Quantitative Assays for Serum PSA Obtained by MRM$^3$ with External or Internal Calibration or by ELISA The patient sera, of which the assaying by MRM$^3$ with external or internal calibration was set out, respectively, in examples 1 and 2, are assayed by ELISA, on the one hand, using the Vidas® TPSA kit (bioMérieux, Marcy l'Etoile, France) and the Vidas® automated analyzer and, on the other hand, using the total PSA kit and the Modular Analytics E170 automated analyzer from the company Roche Diagnostics (Mannheim, Germany). In both cases, the protocol described by the supplier is implemented. These sera correspond to patients suffering from prostate cancer (PCa) or from benign prostatic hypertrophy (BPH). The comparison of the doses obtained according to these three assay methods is established as shown in TABLE 7:

TABLE 7

| Patients | Pathological condition | Concentration established by MRM$^3$ with external calibration (ng/ml) | Concentration established by MRM$^3$ with internal calibration (ng/ml) | Concentration 1 established by ELISA with the Vidas ® TPSA kit (ng/ml) | Concentration 2 established by ELISA with the Roche Total PSA kit (ng/ml) |
| --- | --- | --- | --- | --- | --- |
| B2004 | BPH | 8.07 | 9.24 | 7.89 | 7.03 |
| D4003 | PCa | 3.01 | 3.6 | 5.72 | 5.2 |
| D4004 | BPH | 5.77 | 7.27 | 8.23 | 7.3 |

The doses, determined using the MRM$^3$ methods with external or internal calibration, therefore result in PSA concentrations that are extremely close to those established by means of the conventional ELISA methods.

It should be noted, in this respect, that the ELISA assays do not assay all the PSA molecules present in the blood stream. This is because PSA forms complexes with certain blood anti-proteases, such as alpha-1 anti-chymotrypsin (ACT) and alpha-2 macroglobulin (A2M). The A2M-bound PSA is not detectable by ELISA, whereas it can be assayed by mass spectrometry, as has been established by T. Fortin et al. (MCP, 2008 E-pub). The PSA-A2M complex accounts for approximately 10% of total PSA, but this amount may be modulated according to the pathological condition of the patient. This particular property of PSA explains part of the differences in amounts observed between ELISA and MRM$^3$ techniques.

EXAMPLE 4

Quantitative Assaying of *Treponema pallidum* Recombinant Proteins in a Human Serum This example is carried out with 2 proteins from *Treponema pallidum*, an infectious agent responsible for syphilis, expressed recombinantly (bioMérieux, Marcy l'Etoile, France). In order to facilitate the in vitro expression and the purification of the recombinant proteins, the native sequence of the *Treponema pallidum* proteins was modified by the supplier. The exact sequences of the 2 proteins used are provided below:

TP435 SYPHILIS SEQUENCE
SEQ ID No 51:
MRGSACVSCTTVCPHAGKAKAEKVECALKGGIFRGTLPAADCPGIDTTV

TFNADGTAQKVELALEKKSAPSPLTYRGTWMVREDGIVELSLVSSEQSK

APHEKELYELIDSNSVRYMGAPGAGKPSKEMAPFYVLKKTKKGSSKYKY

HHHHH

TP574 SYPHILIS SEQUENCE
SEQ ID No 52:
MRGSAHHETHYGYATLSYADYWAGELGQSRDVLLAGNAEADRAGDLDAG

MFDAVSRATHGHGAFRQQFQYAVEVLGEKVLSKQETEDSRGRKKWEYET

```
DPSVTKMVRASASFQDLGEDGEIKFEAVEGAVALADRASSFMVDSEEYK

ITNVKVHGMKFVPVAVPHELKGIAKEKFHFVEDSRVTENTNGLKTMLTE

DSFSARKVSSMESPHDLVVDTVGTGYHSRFGSDAEASVMLKRADGSELS

HREFIDYVMNFNTVRYDYYGDDASYTNLMASYGTKHSADSWWKTGRVPR

ISCGINYGFDRFKGSGPGYYRLTLIANGYRDVVADVRFLPKYEGNIDIG

LKGKVLTIGGADAETLMDAAVDVFADGQPKLVSDQAVSLGQNVLSADFT

PGTEYTVEVRFKEFGSVRAKVVAQSSKYKTHHHHHH
```

The amount of recombinant protein is established for Tp435 and Tp574 by protein assay according to the Bradford method (Bradford, M. M. (1976) *A Rapid and Sensitive Method for the Quantitation of Microgram Quantities of Protein Utilizing the Principle of Protein-Dye Binding*. Anal. Biochem. 72: 248-254) using the "Protein Assay" reagent from the company Bio-Rad (Hercules, Calif., United States of America).

The Tp435 protein batch thus has an amount of 0.97 mg/ml. The Tp574 protein batch thus has an amount of 1.4 mg/ml.

The Tp435 and Tp574 recombinant proteins are digested in the following way:

An amount of 80 µg of each protein is sampled and 50 mM ammonium bicarbonate buffer, pH=8.0, is added so as to obtain a final volume of 400 µl.
100 µl of 150 mM DTT are added.
Incubation is carried out at 95° C. for 20 minutes.
Incubation is carried out at 60° C. for 20 minutes.
The samples are cooled to ambient temperature.
100 µl of 150 mM iodoacetamide are added.
Incubation is carried out for 40 minutes at ambient temperature in the dark.
4 µg of trypsin are added.
Incubation is carried out for 4 hours at 37° C.
At the end of digestion, the concentration of each protein digest is 133.3 µg/ml.

Eight volumes of 100 µl of serum from reputedly "healthy" patients (Etablissement Français du Sang [French Blood Bank]) are digested in parallel according to the following protocol:

Each volume of 100 µl of serum is diluted in 3 ml of 50 mM ammonium bicarbonate, pH=8.0.
DTT is added so as to obtain a final concentration of 15 mM.
Reduction is carried out at 60° C. for 40 minutes.
The tubes are cooled to ambient temperature.
Iodoacetamide is added so as to obtain a final concentration of 25 mM.
Alkylation is carried out for 40 minutes at ambient temperature and in the dark.
Trypsin is added with a mass ratio of 1/30.
Digestion is carried out at 37° C. for 4 hours.
DTT is again added so as to obtain a final concentration of 10 mM.
Reduction is carried out at 60° C. for 40 minutes.
The tubes are cooled to ambient temperature.
Iodoacetamide is again added so as to obtain a final concentration of 15 mM.
Alkylation is carried out at ambient temperature and in the dark.
Trypsin is again added with a ratio of 1/30.
Digestion is carried out at 37° C. overnight.
The samples are acidified with formic acid (i.e. 0.1% final concentration).
The Waters Oasis HLB columns are equilibrated with 1 ml of methanol, then 1 ml of "ultrapure" water/0.1% formic acid.
The sample is loaded and is left to flow by gravity.
Washing is carried out with 1 ml of a water/0.1% formic acid mixture.
Elution is carried out with 1 ml of 80% methanol in a water/0.1% formic acid mixture.
The tubes are dried in an evaporator of SpeedVac® SPD2010 type (Thermo Electron Corporation, Waltham, Mass., United States of America) for 1 hour until a volume of approximately 500 µl is obtained.
The 8 tubes of treated sera are mixed so as to obtain a homogeneous digested serum pool.

The following calibration ranges are prepared:

50 µl of Tp574 protein at 133.3 µg/ml is added to 50 µl of Tp435 protein at 133.3 µg/ml. The whole mixture is added to 400 µl of water to which 0.1% formic acid has been added, so as to form a stock solution with a concentration of 26.6 µg/ml for each of the Tp574 and Tp435 proteins (stock solution). A volume of 75 µl of the stock solution is then diluted in 125 µl of water to which 0.1% formic acid has been added, so as to have a solution at 10 000 ng/ml per protein.
37.5 µl of the stock solution are diluted in 162.5 µl of water to which 0.1% formic acid has been added, so as to obtain a solution at 5000 mg/ml
20 µl of the solution at 10 µg/ml are diluted in 180 µl of water so as to have a solution at 1000 ng/ml
20 µl of the solution at 1 µg/ml are diluted in 180 µl of water so as to have a solution at 100 ng/ml
20 µl of the solution at 100 ng/ml are diluted in 180 µl of water so as to have a solution at 10 ng/ml
20 µl of the solution at 5 µg/ml are diluted in 180 µl of water so as to have a solution at 500 ng/ml
20 µl of the solution at 500 ng/ml are diluted in 180 µl of water so as to have a solution at 50 ng/ml
7 fractions of digested serum, each corresponding to 100 µl of serum before digestion, are supplemented, with respectively, 10 µl of each of the solutions between 10 000 and 50 ng/ml so as to obtain a standard range with points at 1, 5, 10, 50, 100, 500 and 1000 ng/ml.
The final serum fraction is supplemented with 10 µl of water, in order to obtain a range point at 0 ng/ml.

The samples and the range points are analyzed with the following chromatographic parameters and with 2 periods having different settings for the mass spectrometer.

Ultimate 3000 chromatography system from the company Dionex (Sunnyvale, Calif., United States of America)
Waters Symmetry C18 column, 2.1 mm internal diameter, 100 mm long, particle size 3.5 µm
Solvent A: $H_2O$+0.1% formic acid
Solvent B: ACN+0.1% formic acid
HPLC gradient defined in TABLE 8 hereinafter:

TABLE 8

| Time | Flow rate (µl) | Solvent A (%) | Solvent B (%) |
|---|---|---|---|
| 0 | 300 | 95 | 5 |
| 3 | 300 | 95 | 5 |
| 28 | 300 | 60 | 40 |
| 30 | 300 | 0 | 100 |
| 38 | 300 | 0 | 100 |
| 38.1 | 300 | 95 | 5 |
| 48 | 300 | 95 | 5 |

Period 1 corresponds to the monitoring of the proteotypic peptide SAPSPLTYR (SEQ ID No 53) of the Tp435 protein. Period 2 corresponds to the monitoring of the proteotypic peptide FVPVAVPHELK (SEQ ID No 54) of the Tp574 protein.

For each proteotypic peptide, doubly-charged first-generation fragments comprising a proline in position 1 are selected and fragmented, according to the following machine parameters:

Period 1 for the Tp435 protein:
The machine parameters are the same as for example 1, with the exception of the following parameters:
Precursor: 496.50 Da
$1^{st}$-generation ion: 417.50 Da
Q3 input barrier: 4.00 V
Mass at start of scan (Da): 430.00 Da
Mass at end of scan (Da): 750.00 Da
Time (s): 0.0320 s
Trapping radiofrequency amplitude, start: 2.88
Trapping radiofrequency amplitude, end: 4.10
Ion trap output voltage (start) −142.07 V
Ion trap output voltage (end) −129.13 V
Source temperature: 450.00° C.
Heating gas: 50.00 psi
Declustering potential: 80.00 V
Collision energy: 18.00 eV
Excitation energy (AF2): 0.12

Period 2 for the Tp574 protein:
The machine parameters are the same as for period 1, with the exception of the following parameters:
Precursor: 618.40 Da
$1^{st}$-generation ion: 495.50 Da
Mass at start of scan (Da): 500.00 Da
Mass at end of scan (Da): 850.00 Da
Time (s): 0.0350 s
Trapping radiofrequency amplitude, start: 3.15
Trapping radiofrequency amplitude, end: 4.48
Ion trap output voltage (start)-139.24 V
Ion trap output voltage (end)-125.09 V
Declustering potential: 90.00 V
Collision energy: 25.00 eV
Excitation energy (AF2): 0.09

The measurement of the signal of the sum of the y3 and y5 ions (m/z 649.4 and 439.4) of the proteotypic peptide SAPSPLTYR (SEQ ID No 53) of the Tp435 protein, for the range points having an amount of between 5 and 50 ng/ml, made it possible to obtain TABLE 9 hereinafter:

TABLE 9

| Concentration (ng/ml) | Area of the peak | Signal to noise | Quantification limit (ng/ml) |
|---|---|---|---|
| 5 | 1.82E+05 | 1 | 28.4 |
| 10 | 1.55E+05 | 1 | |
| 50 | 2.05E+06 | 17.6 | |

The measurement of the signal of the sum of the y5 and y7 ions (m/z 623.4 and 793.4) of the proteotypic peptide FVPVAVPHELK (SEQ ID No 54) of the Tp574 protein, for the range points having an amount of between 5 and 50 ng/ml, made it possible to obtain TABLE 10 hereinafter:

TABLE 10

| Concentration (ng/ml) | Area of the peak | Signal to noise | Quantification limit (ng/ml) |
|---|---|---|---|
| 5 | 6.14E+05 | 6.3 | 8.7 |
| 10 | 2.58E+06 | 11.5 | |
| 50 | 1.92E+07 | 61.9 | |

Figure 4A:
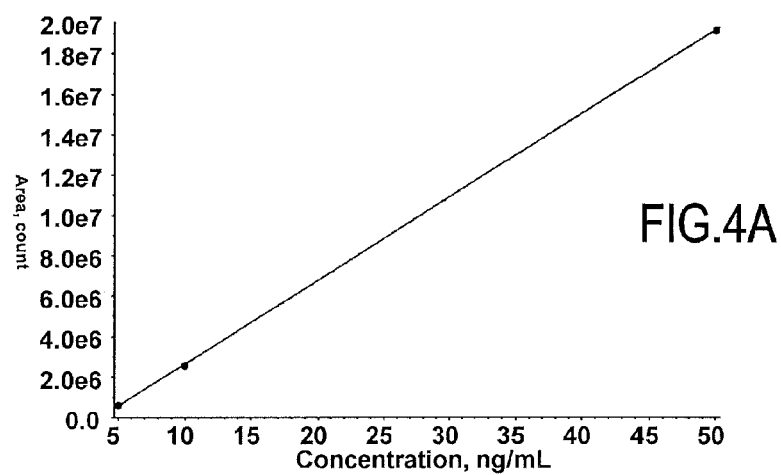
Figure 4B:
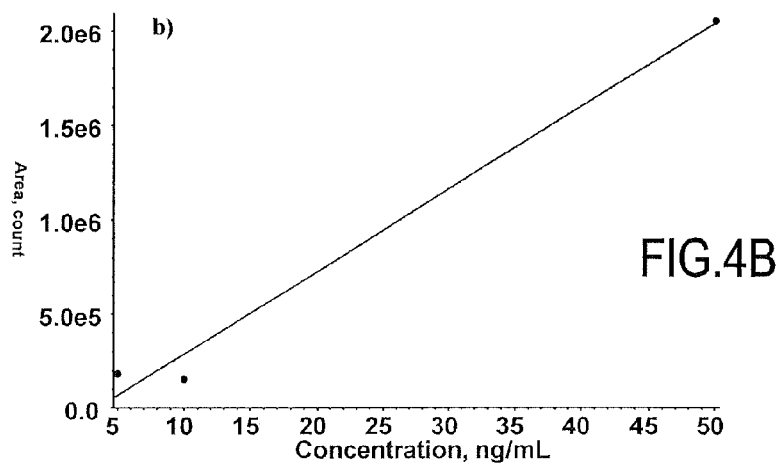

These results make it possible to establish the calibration curves for the Tp435 and Tp574 proteins respectively represented in FIGS. 4A and 4B.

These curves are modeled using linear regression in the form of equations which make it possible to calculate the Tp435 and Tp574 concentration for any human serum sample having an unknown amount of Tp435 or of Tp574.

The Tp435 concentration is calculated by virtue of the equation:

$$y=4.14\times10^5 X-1.5\times10^6.$$

The Tp574 concentration is calculated by virtue of the equation:

$$y=4.38\times10^4 X-1.5\times10^5.$$

EXAMPLE 5

Improvement in Performance Levels of the Quantitative Assays with the MRM³ Method Using Double-Charged Ions as First-Generation Fragment The analytical performance levels obtained in example 4 are compared, under the same sample treatment conditions, with the performance levels obtained with a conventional MRM assay or with an MRM³ assay not using a double-charged first-generation fragment. For each protein, the same proteotypic peptide is assayed by means of the three methods, namely the peptide LSEPAELTDAVK (SEQ ID No 50) for PSA, the peptide SAPSPLTYR (SEQ ID No 53) for the Tp435 protein and the peptide FVPVAVPHELK (SEQ ID No 54) for the Tp574 protein.

The analysis is carried with samples prepared according to the protocol of example 4 with a stock solution comprising 50 μl of Tp574 at 133.3 μg/ml, plus 50 μl of Tp435 protein at 133.3 μg/ml, plus 50 μl of PSA protein at 133.3 μg/ml, plus 350 μl of water to which 0.1% formic acid has been added.

The MRM³ analysis with double-charged first-generation fragments is carried out with the chromatography and mass spectrometry method described in example 4 for the three proteins. The mass spectrometer settings are established on three periods corresponding to the settings suitable for each proteotypic peptide. This assay is called method 1 for this example.

The MRM³ analysis with singly-charged first-generation fragments is carried out with the ions y9 (943.5 m/z) for the proteotypic peptide of PSA having an m/z 636.8, y5 (649.2 m/z) for the proteotypic peptide of Tp435 having an m/z 496.8 and y5 (623.3 m/z) for the proteotypic peptide of Tp574 having an m/z 618.8. The chromatographic peak is obtained by adding together the signal of the second-generation fragments having an m/z 609+627+646+698 for the proteotypic peptide of PSA, 631.2+457.4+475.4 for the proteotypic peptide of Tp435 and 477.5+364.2+605.4 for the proteotypic peptide of Tp574. This assay is called method 2 for this example.

For method 2, the operating of the mass spectrometer is divided up into 3 periods.

Period 1 for PSA:

The machine parameters are the same as for example 1, with the exception of the following parameters:
Precursor: 636.80 Da
$1^{st}$-generation ion: 943.50 Da
Mass at start of scan (Da): 600.00 Da
Mass at end of scan (Da): 800.00 Da
Time (s): 0.0200 s
Trapping radiofrequency amplitude, start: 3.53
Trapping radiofrequency amplitude, end: 4.29
Ion trap output voltage (start) −135.20 V
Ion trap output voltage (end) −127.11 V
Source temperature: 450.00° C.
Heating gas: 50.00 psi
Declustering potential: 120.00 V
Input potential before Q0: 4.00 V
Collision energy: 23.00 eV
Excitation energy (AF2): 0.12

Period 2 for the Tp435 protein:

The machine parameters are the same as for period 1, with the exception of the following parameters:
Precursor: 496.50 Da
$1^{st}$-generation ion: 649.20 Da
Q3 input barrier: 4.00 V
Mass at start of scan (Da): 430.00 Da
Mass at end of scan (Da): 640.00 Da
Time (s): 0.0210 s
Trapping radiofrequency amplitude, start: 2.88
Trapping radiofrequency amplitude, end: 3.68
Ion trap output voltage (start) −142.07 V
Ion trap output voltage (end) −133.58 V
Declustering potential: 80.00 V
Collision energy: 23.00 eV
Excitation energy (AF2): 0.12

Period 3 for the Tp574 protein:

The machine parameters are the same as for period 1, with the exception of the following parameters:
Precursor: 618.40 Da
$1^{st}$-generation ion: 623.30 Da
Q3 input barrier: 4.00 V
Mass at start of scan (Da): 350.00 Da
Mass at end of scan (Da): 620.00 Da
Time (s): 0.0270 s
Trapping radiofrequency amplitude, start: 2.58
Trapping radiofrequency amplitude, end: 3.60
Ion trap output voltage (start) −145.30 V
Ion trap output voltage (end) −134.39 V
Collision energy: 35.00 eV
Excitation energy (AF2): 0.10

The MRM analysis is carried out with the ions y9 (943.5 m/z) for the proteotypic peptide of PSA having an m/z 636.8, y5 (649.2 m/z) for the proteotypic peptide of Tp435 having an m/z 496.8 and y5 (623.3 m/z) for the proteotypic peptide of Tp574 having an m/z 618.8. This assay is called method 3 for this example.

For method 3, the mass spectrometer parameters are the following:
Scan type: MRM (MRM)
Polarity: Positive
Ionization source: Turbo V™ (Applied BioSystems)
Q1 setting: Filtering with unit resolution
Q3 setting: Filtering with unit resolution
Pause between two scans: 5.007 ms
Q1 mass (Da) 496.20
Q3 mass (Da) 649.30
Scan time 30.00
Declustering potential 110 V
Collision energy 25 eV
Collision cell output potential 10 V
Q1 mass (Da) 636.8
Q3 mass (Da) 943.5
Scan time 35.00
Declustering potential 115 V
Collision energy 23 eV
Collision cell output potential 22 V
Q1 mass (Da) 618.4
Q3 mass (Da) 623.4
Scan time 35.00
Declustering potential 120 V
Collision energy 29 eV
Collision cell output potential 10 V
Curtain gas: 50.00 psi
Cone voltage: 5500.00 V
Source temperature: 500.00° C.
Nebulizing gas: 50.00 psi
Heating gas: 40.00 psi
Collision cell filling 9.00 (arbitrary unit)
Input potential before Q0 5.00 V The limit of quantification of the 3 proteins is determined by calculating the amount of protein for which a ratio of the signal divided by the background noise of 10 is obtained, as presented in TABLE 11.

TABLE 11

| | Method 1 | | Method 2 | | Method 3 | |
|---|---|---|---|---|---|---|
| Proteins | Signal to noise of the peak at 50 ng/ml | Limit of quantification (in ng/ml) on double-charged first-generation ion | Signal to noise of the peak at 50 ng/ml | Limit of quantification (in ng/ml) on singularly-charged first-generation ion | Signal to noise of the peak at 50 ng/ml | Limit of quantification (in ng/ml) by MRM |
| TP574 | 57.5 | 8.7 | 6.4 | 78.1 | 3.2 | 156.3 |
| TP435 | 17.6 | 28.4 | 4.3 | 116.3 | 11.9 | 42.0 |
| PSA | 34.8 | 14.4 | 16.1 | 31.1 | 19.4 | 25.8 |

The limits of quantification obtained with the method described in the present invention are much lower than those obtained with methods 2 and 3. The present invention therefore results in a quantitative assay that is more sensitive than the other methods.

EXAMPLE 6

Collision Enemy Optimization

The choice of the precursor ion and of the first-generation fragment for carrying out the MRM$^3$ is essential. The most intense first-generation fragment does not necessarily have to be chosen. In the context of the invention, it has been demonstrated that double-charged ions having a proline or a histidine exhibit a more specific fragmentation and generate fewer secondary fragmentations in $MS^3$ and that they are much more suitable for obtaining the most effective quantitative assay.

By way of example, the collision energy of the proteotypic peptide SAPSPLTYR (SEQ ID No 53) of the Tp435 protein was optimized.

A volume of 50 µl of the Tp435 protein is digested, desalified on a Waters Oasis HLB column and added to 300 µl of a mixture of ACN/water 50/50 plus 0.1% formic acid. The mixture is then infused into the mass spectrometer with a flow rate of 10 µl/minute.

Figure 5A:
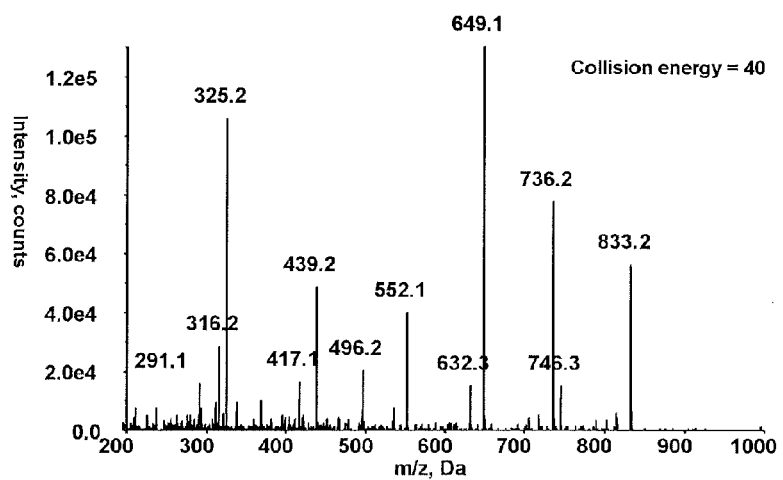
FIGS. 5A, 5B and 5C are various mass spectra obtained with various collision energies, respectively 40, 35 and 30 eV.
Figure 5B:
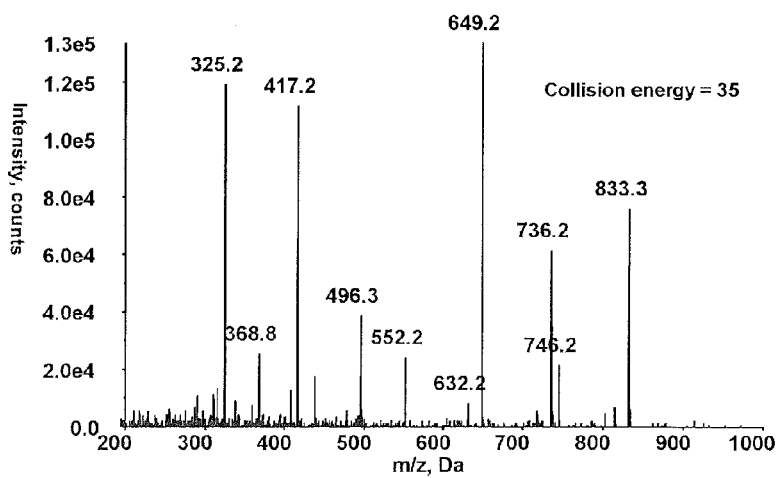
Figure 5C:
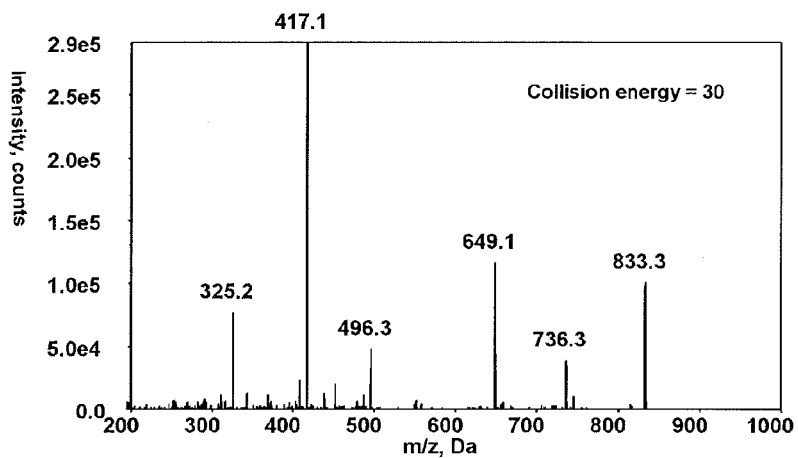

The machine parameters are the following:
Scan type: Enhanced product ion (or EPI)
Polarity: Positive
Scan mode: Profile
Ionization source: Turbo V (Applied Biosystems)
Precursor: 496.20 Da
Resolution in Q1: Unit
Scan speed: 10000 Da/s
Trapping in Q0: No
Linear ion trap filling time in Q3: 1.00 ms
Dynamic filling: Active
TIC Target EMS Scan: $10.00 \times 10^7$ counts
TIC Target: $10.00 \times 10^7$ counts
Maximum filling time: 250.000 ms
Minimum filling time: 0.050 ms
Filling time by default: 1.000 ms
Q3 input voltage: 8.00 V
Ion trap scan increment in Q3: 0.12 Da
Mass at start of scan (Da): 200.00 Da
Mass at end of scan (Da): 667.01 Da
Time (s): 0.0467 s
Trapping radiofrequency amplitude, start: 2.19
Trapping radiofrequency amplitude, end: 3.82
Ion trap output voltage (start): −149.35 V
Ion trap output voltage (end): −125.68 V
Mass at start of scan (Da): 667.01 Da
Mass at end of scan (Da): 1000 Da
Time (s): 0.0333 s
Trapping radiofrequency amplitude, start: 3.82
Trapping radiofrequency amplitude, end: 4.99
Ion trap output voltage (start): −125.68 V
Ion trap output voltage (end): −108.80 V
Curtain gas: 30.00 psi
Cone voltage: 5500.00 V
Source temperature: Ambient temperature
Nebulizing gas: 18.00 psi
Heating gas: Ambient temperature
Collision cell filling: High
Declustering potential: 100.00 V
Input potential before Q0: 10.00 V
Collision energy: between 5 and 60 eV When configuring the collision energy at 40 eV (FIG. 5A), it is observed that the fragment 417.2, corresponding to the double-charged first-generation fragment containing a proline in the N-terminal position, is not very intense compared with a fragmentation with a collision energy of 35 or of 30 eV (respectively FIGS. 5B and 5C). When the intensity of the first-generation fragment 417.2 decreases, the intensity of the other fragments increases. It is therefore tempting to use a collision energy of 40 eV while choosing the most intense first-generation fragment, i.e. that of 649.5 Da corresponding to a singularly-charged first-generation fragment. However, this choice is not optimum, as shown by the optimization of collision energy that can be seen in FIG. 5D.

The optimization of the collision energy is carried out by infusion at 10 µl/min and by varying only the collision energy from 5 to 60 eV. The only difference compared with the previous parameters is the use of a scan mode of MRM type with selection of the mass 496.5 Da in Q1 and of the masses 417.8 or 649.5 in Q3 with a cycle time of 100 s, and also the following adjustment of the parameters:
Nebulizing gas: 35.00
Declustering potential: 80.00
Input potential before Q0: 3.00

Figure 5D:
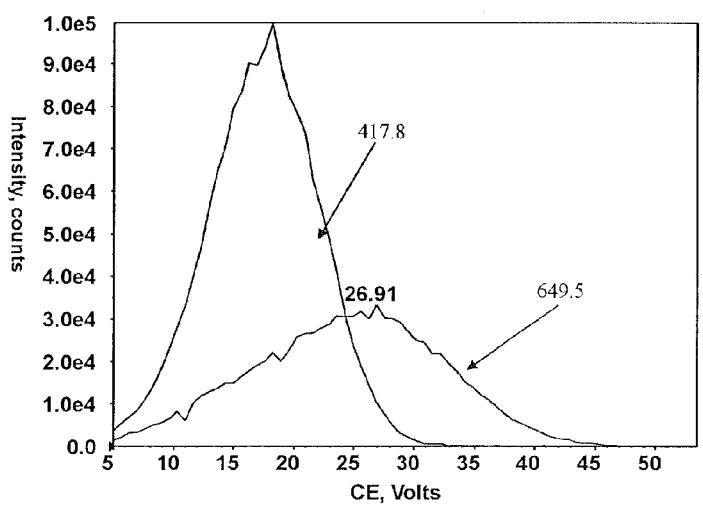
FIG. 5D represents the change in the intensity of the current induced, as a function of the collision energy (CE) used for the formation of the first-generation fragment ions.

The optimization of the collision energy of the transitions 496.3/417.8, corresponding to the double-charged fragment containing a proline in the N-terminal position, and 496.3/649.5, corresponding to the most intense singularly-charged fragment, shows, in FIG. 5D, that the collision energy makes it possible to obtain a significant gain in signal with the transition 496.3/417.8, according to an assay corresponding to example 4.

This gain in signal is reflected by a quantitative assay having better analytical performance levels, characterized by a lower limit of quantification, as shown in TABLE 12.

TABLE 12

| Protein | Limit of quantification (ng/ml) with the singularly-charged first-generation ion | Limit of quantification (ng/ml) with the double-charged first-generation ion |
|---|---|---|
| TP574 | 78.1 | 8.7 |

After optimization of the mass spectrometry parameters, the limit of quantification obtained with the double-charged first-generation ion, according to the method described in the present invention, is much lower than that obtained with the singularly-charged first-generation ion. The method using the double-charged first-generation ion therefore makes it possible to obtain a more sensitive quantification method.

EXAMPLE 7

Improvement in Performance Levels of the Quantitative Assays with the $MRM^3$ Method Using Double-Charged Ions as First-Generation Fragment The fragmentation of the proteotypic peptide SAPSPLTYR (SEQ ID No 53) of the Tp435 protein, which has two prolines, one of which is in position 2, was compared by selecting as first-generation ion either the most intense fragment ion or the fragment ion containing a proline in singularly-charged form, or this same ion in double-charged form.

The most intense singularly-charged first-generation ion is the y5 ion having an m/z 649.2. The first-generation fragment ion containing a proline in singularly-charged or double-charged form is the y7 ion, respectively having an m/z 833.4 for the singularly-charged form and an m/z 417.5 for the double-charged form.

A volume of 50 µl of the Tp435 protein is digested, desalified on a Waters Oasis HLB column and added to 300 µl of a mixture of ACN/water 50/50 plus 0.1% formic acid. The mixture is then infused into the mass spectrometer with a flow rate of 10 µl/minute.

The machine parameters are the following:
For the MS³ of the most intense singularly-charged first-generation ion:
Scan type: MS³
Polarity: Positive
Scan mode: Profile
Ionization source: Turbo V (Applied Biosystems)
Precursor: 496.30 Da
1$^{st}$-generation ion: 649.30 Da
Resolution in Q1: Unit
Scan speed: 10000 Da/s
Trapping in Q0: Yes
Linear ion trap filling time in Q3: 150.00 ms
Dynamic filling: No
Fragmentation: Yes
Excitation time: 25.00 ms
Q3 input voltage: 8.00 V
Ion trap scanning increment in Q3: 0.12 Da
Mass at start of scan (Da): 250.00 Da
Mass at end of scan (Da): 640.00 Da
Trapping radiofrequency amplitude, start: 3.08
Trapping radiofrequency amplitude, end: 4.36
Ion trap output voltage (start): −144.99 V
Ion trap output voltage (end): −122.19 V
Curtain gas: 20.00 psi
Cone voltage: 5500.00 V
Source temperature: Ambient temperature
Nebulizing gas: 35.00 psi
Heating gas: Ambient temperature
Collision cell filling: High
Declustering potential: 110.00 V
Input potential before Q0: 10.00 V
Collision energy: 24 eV
Excitation energy: 0.11 eV
For the MS³ of the singularly-charged first-generation ion y7:
Scan type: MS³
Polarity: Positive
Scan mode: Profile
Ionization source: Turbo V (Applied Biosystems)
Precursor: 496.30 Da
1$^{st}$-generation ion: 833.40 Da
Resolution in Q1: Unit
Scan speed: 10 000 Da/s
Trapping in Q0: Yes
Linear ion trap filling time in Q3: 150.00 ms
Dynamic filling: No
Fragmentation: Yes
Excitation time: 25.00 ms
Q3 input voltage: 8.00 V
Ion trap scan increment in Q3: 0.12 Da
Mass at start of scan (Da): 300.00 Da
Mass at end of scan (Da): 820.00 Da
Trapping radiofrequency amplitude, start: 3.24
Trapping radiofrequency amplitude, end: 4.95
Ion trap output voltage (start): −142.06 V
Ion trap output voltage (end): −111.66 V
Curtain gas: 20.00 psi
Cone voltage: 5500.00 V
Source temperature: Ambient temperature
Nebulizing gas: 35.00 psi
Heating gas: Ambient temperature
Collision cell filling: High
Declustering potential: 110.00 V
Input potential before Q0: 10.00 V
Collision energy: 24 eV
Excitation energy: 0.14 eV
For the MS³ of the double-charged first-generation ion y7:
Scan type: MS³
Polarity: Positive
Scan mode: Profile
Ionization source: Turbo V (Applied Biosystems)
Precursor: 496.30 Da
1$^{st}$-generation ion: 417.50 Da
Resolution in Q1: Unit
Scan speed 10000 Da/s
Trapping in Q0: Yes
Linear ion trap filling time in Q3: 150.00 ms
Dynamic filling: No
Fragmentation: Yes
Excitation time: 25.00 ms
Q3 input voltage: 8.00 V
Ion trap scan increment in Q3: 0.12 Da
Mass at start of scan (Da): 300.00 Da
Mass at end of scan (Da): 850.00 Da
Trapping radiofrequency amplitude, start: 3.24
Trapping radiofrequency amplitude, end: 5.05
Ion trap output voltage (start): −142.06 V
Ion trap output voltage (end): −109.91 V
Curtain gas: 20.00 psi
Cone voltage: 5500.00 V
Source temperature: Ambient temperature
Nebulizing gas: 35.00 psi
Heating gas: Ambient temperature
Collision cell filling: High
Declustering potential: 110.00 V
Input potential before Q0: 10.00 V
Collision energy: 25 eV
Excitation energy: 0.12 eV For the most intense first-generation singularly-charged fragment ion having an m/z equal to 649.2, the fragmentation obtained in MS³ is, as in the previous case, very complex, dividing the signal between all the secondary fragmentation peaks, as shown in FIG. 6A. The most intense peak of the MS³ spectrum corresponds to $3.2 \times 10^5$ counts.

For the singularly-charged first-generation fragment ion y7, having an m/z equal to 833.4, the fragmentation spectrum observed is very complex, containing many secondary fragmentation peaks, as shown in FIG. 6B. The most intense peak of the MS³ spectrum corresponds to $3.8 \times 10^5$ counts.

For the double-charged first-generation ion y7, having an m/z equal to 417.5, the fragmentation obtained is much simpler and the signal is concentrated on 5 major peaks, as shown in FIG. 6C. The signal of the major peak is $7.3 \times 10^6$ counts.

This shows that the choice of the peptide according to the present invention results in a more sensitive assay and explains the gain in sensitivity observed in example 5.

The choice of the first-generation fragment for carrying out the MRM³ is essential. As shown in this example, the most intense first-generation fragment does not necessarily have to be chosen. The choice of the precursor ion is also important. In the context of the invention, it was demonstrated that the doubly-charged precursor ions having two prolines or one proline and one histidine exhibit a more specific fragmentation and generate even fewer secondary fragmentations in MS³, and that they are much more suitable for obtaining the most effective quantitative assay.

The invention claimed is:

1. A method for the quantitative detection of a target protein in a sample, comprising the following steps:
   a) treatment of the sample in order to generate peptides,
   b) quantitative assaying of at least one proteotypic peptide generated from the target protein, via a mass spectrometry technique implementing the following steps i) to vii):
      i) ionizing of the proteotypic peptide to give precursor ions which are filtered according to their mass m/z, and selecting a given precursor ion having a mass $(m/z)_1$ according to the target protein sought,
      ii) fragmenting of the selected precursor ion into first-generation fragment ions,
      iii) filtering the first-generation fragment ions generated according to their mass m/z, and selecting a given first-generation fragment ion having a mass $(m/z)_2$ according to the target protein sought,
      iv) fragmenting the selected first-generation fragment ion into second-generation fragment ions,
      v) detecting of at least a part of the second-generation fragment ions so as to give a series of quantitative measurements,
      vi) selecting of at least one quantitative measurement associated with a second-generation ion, and
      vii) correlating the at least one selected quantitative measurement associated with the second-generation ion to the amount of proteotypic peptide generated and to the amount of target protein present in the sample, with the implementation of a calibration step, wherein said calibration step is performed using a calibration curve or internal calibration with a heavy peptide, wherein said selected quantitative measurement is performed by multiple reaction monitoring$^3$ (MRM$^3$), and wherein said selected first-generation fragment ion having a $(m/z)_2$ is a doubly-charged peptide which has a proline or a histidine in position 1.

2. The method of claim 1, wherein said selected precursor ion having a mass $(m/z)_1$ is a doubly-charged peptide which contains a number n of from 6 to 15 amino acids, and which comprises at least one proline at positions 2 to n−2 and/or one histidine at positions 1 to n−2.

3. The method of claim 2, wherein said selected precursor ion having a mass $(m/z)_1$, comprises at least 2 prolines or one proline and one histidine.

4. The method of claim 1, wherein said quantitative assaying of the generated peptides by mass spectrometry is preceded by a separation of the peptides by chromatography or electrophoresis of the peptides generated in step a).

5. The method of claim 4, wherein the separation by chromatography comprises reverse-phase chromatography.

6. The method of claim 1, wherein said treatment of the sample is carried out by digestion with a protease enzyme.

7. The method of claim 1, wherein in step v), the intensity of the current induced by at least part of the second-generation fragment ions is detected as a function of time, and the signal obtained over a given period is broken down into a mass spectrum of the various ions present according to their mass m/z, so as to obtain a mass peak associated with each of the second generation ions detected present over said given period, and the signal corresponding to the current of at least one second-generation ion selected is recomposed, and the intensity of the corresponding current measured is the quantitative measurement selected in step vi).

8. The method claim 7, wherein in step vi), the quantitative measurement associated with the second-generation fragment ion having the most intense peak m/z over said given period is selected.

9. The method of claim 7, wherein in step vii), the correlation is performed on the basis of the sum of at least two quantitative measurements, each being associated with the second-generation fragment ions having the most intense peaks m/z over the given period.

10. The method of claim 6, wherein said protease enzyme is trypsin.

* * * * *

SEQUENCE LISTING

<160> NUMBER OF SEQ ID NOS: 54

<210> SEQ ID NO 1
<211> LENGTH: 7
<212> TYPE: PRT
<213> ORGANISM: artificial sequence
<220> FEATURE:
<223> OTHER INFORMATION: OATP2B1

<400> SEQUENCE: 1

Val Leu Leu Gln Thr Leu Arg
1               5

<210> SEQ ID NO 2
<211> LENGTH: 6
<212> TYPE: PRT
<213> ORGANISM: ARTIFICIAL SEQUENCE
<220> FEATURE:
<223> OTHER INFORMATION: OATP2B1

<400> SEQUENCE: 2

Leu Leu Gln Thr Leu Arg
1               5

<210> SEQ ID NO 3
<211> LENGTH: 5
<212> TYPE: PRT
<213> ORGANISM: artificial sequence
<220> FEATURE:
<223> OTHER INFORMATION: OATP2B1

<400> SEQUENCE: 3

Leu Gln Thr Leu Arg
1               5

<210> SEQ ID NO 4
<211> LENGTH: 16
<212> TYPE: PRT
<213> ORGANISM: artificial sequence
<220> FEATURE:
<223> OTHER INFORMATION: IFN-alpha4

<400> SEQUENCE: 4

His Asp Phe Gly Phe Pro Gln Glu Glu Phe Gly Asn Gln Phe Gln Lys
1               5                   10                  15

<210> SEQ ID NO 5
<211> LENGTH: 15
<212> TYPE: PRT
<213> ORGANISM: artificial sequence
<220> FEATURE:
<223> OTHER INFORMATION: IFN-alpha4

<400> SEQUENCE: 5

Asp Phe Gly Phe Pro Gln Glu Glu Phe Gly Asn Gln Phe Gln Lys
1               5                   10                  15

<210> SEQ ID NO 6
<211> LENGTH: 10
<212> TYPE: PRT
<213> ORGANISM: artificial sequence
<220> FEATURE:
<223> OTHER INFORMATION: IFN-alpha4

<400> SEQUENCE: 6

Tyr Ser Pro Cys Ala Trp Glu Val Val Arg
1               5                   10

```
<210> SEQ ID NO 7
<211> LENGTH: 8
<212> TYPE: PRT
<213> ORGANISM: artificial sequence
<220> FEATURE:
<223> OTHER INFORMATION: IFN-alpha4

<400> SEQUENCE: 7

Pro Cys Ala Trp Glu Val Val Arg
1               5

<210> SEQ ID NO 8
<211> LENGTH: 14
<212> TYPE: PRT
<213> ORGANISM: artificial sequence
<220> FEATURE:
<223> OTHER INFORMATION: Plastin-1

<400> SEQUENCE: 8

Gln Phe Val Thr Pro Ala Asp Val Val Ser Gly Asn Pro Lys
1               5                   10

<210> SEQ ID NO 9
<211> LENGTH: 10
<212> TYPE: PRT
<213> ORGANISM: artificial sequence
<220> FEATURE:
<223> OTHER INFORMATION: Plastin-1

<400> SEQUENCE: 9

Glu Ala Ser Leu Pro Leu Pro Gly Tyr Lys
1               5                   10

<210> SEQ ID NO 10
<211> LENGTH: 9
<212> TYPE: PRT
<213> ORGANISM: artificial sequence
<220> FEATURE:
<223> OTHER INFORMATION: Plastin-1

<400> SEQUENCE: 10

Leu Ser Pro Glu Glu Leu Leu Leu Arg
1               5

<210> SEQ ID NO 11
<211> LENGTH: 9
<212> TYPE: PRT
<213> ORGANISM: artificial sequence
<220> FEATURE:
<223> OTHER INFORMATION: Ezrin

<400> SEQUENCE: 11

Ile Gly Phe Pro Trp Ser Glu Ile Arg
1               5

<210> SEQ ID NO 12
<211> LENGTH: 8
<212> TYPE: PRT
<213> ORGANISM: artificial sequence
<220> FEATURE:
<223> OTHER INFORMATION: Aminoacylase 1

<400> SEQUENCE: 12

Val Ala Pro Asp Val Asp Phe Lys
1               5
```

```
<210> SEQ ID NO 13
<211> LENGTH: 11
<212> TYPE: PRT
<213> ORGANISM: artificial sequence
<220> FEATURE:
<223> OTHER INFORMATION: L-FABP

<400> SEQUENCE: 13

Ala Ile Gly Leu Pro Glu Glu Leu Ile Gln Lys
1               5                   10

<210> SEQ ID NO 14
<211> LENGTH: 17
<212> TYPE: PRT
<213> ORGANISM: artificial sequence
<220> FEATURE:
<223> OTHER INFORMATION: Protein disulfide isomerase

<400> SEQUENCE: 14

His Asn Gln Leu Pro Leu Val Ile Glu Phe Thr Glu Gln Thr Ala Pro
1               5                   10                  15

Lys

<210> SEQ ID NO 15
<211> LENGTH: 13
<212> TYPE: PRT
<213> ORGANISM: artificial sequence
<220> FEATURE:
<223> OTHER INFORMATION: Protein disulfide isomerase

<400> SEQUENCE: 15

Asp Ala Pro Glu Glu Glu Asp His Val Leu Val Leu Arg
1               5                   10

<210> SEQ ID NO 16
<211> LENGTH: 12
<212> TYPE: PRT
<213> ORGANISM: artificial sequence
<220> FEATURE:
<223> OTHER INFORMATION: Protein disulfide isomerase

<400> SEQUENCE: 16

Tyr Lys Pro Glu Ser Glu Glu Leu Thr Ala Glu Arg
1               5                   10

<210> SEQ ID NO 17
<211> LENGTH: 9
<212> TYPE: PRT
<213> ORGANISM: artificial sequence
<220> FEATURE:
<223> OTHER INFORMATION: Protein disulfide isomerase

<400> SEQUENCE: 17

Thr His Ile Leu Leu Phe Leu Pro Lys
1               5

<210> SEQ ID NO 18
<211> LENGTH: 8
<212> TYPE: PRT
<213> ORGANISM: artificial sequence
<220> FEATURE:
<223> OTHER INFORMATION: Protein disulfide isomerase

<400> SEQUENCE: 18

Gln Leu Ala Pro Ile Trp Asp Lys
1               5
```

```
<210> SEQ ID NO 19
<211> LENGTH: 8
<212> TYPE: PRT
<213> ORGANISM: artificial sequence
<220> FEATURE:
<223> OTHER INFORMATION: Protein disulfide isomerase

<400> SEQUENCE: 19

Val His Ser Phe Pro Thr Leu Lys
1               5

<210> SEQ ID NO 20
<211> LENGTH: 8
<212> TYPE: PRT
<213> ORGANISM: artificial sequence
<220> FEATURE:
<223> OTHER INFORMATION: Protein disulfide isomerase

<400> SEQUENCE: 20

Phe Phe Pro Ala Ser Ala Asp Arg
1               5

<210> SEQ ID NO 21
<211> LENGTH: 8
<212> TYPE: PRT
<213> ORGANISM: artificial sequence
<220> FEATURE:
<223> OTHER INFORMATION: Protein disulfide isomerase

<400> SEQUENCE: 21

Ala Leu Ala Pro Glu Tyr Ala Lys
1               5

<210> SEQ ID NO 22
<211> LENGTH: 7
<212> TYPE: PRT
<213> ORGANISM: artificial sequence
<220> FEATURE:
<223> OTHER INFORMATION: Protein disulfide isomerase

<400> SEQUENCE: 22

Glu Glu Cys Pro Ala Val Arg
1               5

<210> SEQ ID NO 23
<211> LENGTH: 18
<212> TYPE: PRT
<213> ORGANISM: artificial sequence
<220> FEATURE:
<223> OTHER INFORMATION: Keratin, type 1 cytoskeletal 20

<400> SEQUENCE: 23

Ser Leu Ser Ser Ser Leu Gln Ala Pro Val Val Ser Thr Val Gly Met
1               5                   10                  15

Gln Arg

<210> SEQ ID NO 24
<211> LENGTH: 11
<212> TYPE: PRT
<213> ORGANISM: artificial sequence
<220> FEATURE:
<223> OTHER INFORMATION: Keratin, type 1 cytoskeletal 20

<400> SEQUENCE: 24

Glu Ser Leu Glu His Thr Leu Glu Glu Thr Lys
```

<210> SEQ ID NO 25
<211> LENGTH: 14
<212> TYPE: PRT
<213> ORGANISM: artificial sequence
<220> FEATURE:
<223> OTHER INFORMATION: Keratin, type 1 cytoskeletal 20

<400> SEQUENCE: 25

Leu Gly Thr Thr Pro Ser Val Tyr Gly Gly Ala Gly Gly Arg
1               5                   10

<210> SEQ ID NO 26
<211> LENGTH: 9
<212> TYPE: PRT
<213> ORGANISM: artificial sequence
<220> FEATURE:
<223> OTHER INFORMATION: Keratin, type 1 cytoskeletal 20

<400> SEQUENCE: 26

Gln Trp Tyr Glu Thr Asn Ala Pro Arg
1               5

<210> SEQ ID NO 27
<211> LENGTH: 9
<212> TYPE: PRT
<213> ORGANISM: artificial sequence
<220> FEATURE:
<223> OTHER INFORMATION: Keratin, type 1 cytoskeletal 20

<400> SEQUENCE: 27

Val Phe Asp Asp Leu Thr Leu His Lys
1               5

<210> SEQ ID NO 28
<211> LENGTH: 9
<212> TYPE: PRT
<213> ORGANISM: artificial sequence
<220> FEATURE:
<223> OTHER INFORMATION: 14-3-3 sigma protein

<400> SEQUENCE: 28

Glu Met Pro Pro Thr Asn Pro Ile Arg
1               5

<210> SEQ ID NO 29
<211> LENGTH: 9
<212> TYPE: PRT
<213> ORGANISM: artificial sequence
<220> FEATURE:
<223> OTHER INFORMATION: S100-A11 protein Calgizarin

<400> SEQUENCE: 29

Ile Ser Ser Pro Thr Glu Thr Glu Arg
1               5

<210> SEQ ID NO 30
<211> LENGTH: 7
<212> TYPE: PRT
<213> ORGANISM: artificial sequence
<220> FEATURE:
<223> OTHER INFORMATION: S100-A11 protein Calgizarin

<400> SEQUENCE: 30

Asp Pro Gly Val Leu Asp Arg
1               5

```
<210> SEQ ID NO 31
<211> LENGTH: 10
<212> TYPE: PRT
<213> ORGANISM: artificial sequence
<220> FEATURE:
<223> OTHER INFORMATION: Plastin-1

<400> SEQUENCE: 31

Pro Ala Asp Val Val Ser Gly Asn Pro Lys
1               5                   10

<210> SEQ ID NO 32
<211> LENGTH: 6
<212> TYPE: PRT
<213> ORGANISM: artificial sequence
<220> FEATURE:
<223> OTHER INFORMATION: Plastin-1

<400> SEQUENCE: 32

Pro Leu Pro Gly Tyr Lys
1               5

<210> SEQ ID NO 33
<211> LENGTH: 7
<212> TYPE: PRT
<213> ORGANISM: artificial sequence
<220> FEATURE:
<223> OTHER INFORMATION: Plastin-1

<400> SEQUENCE: 33

Pro Glu Glu Leu Leu Leu Arg
1               5

<210> SEQ ID NO 34
<211> LENGTH: 6
<212> TYPE: PRT
<213> ORGANISM: artificial sequence
<220> FEATURE:
<223> OTHER INFORMATION: Ezrin

<400> SEQUENCE: 34

Pro Trp Ser Glu Ile Arg
1               5

<210> SEQ ID NO 35
<211> LENGTH: 6
<212> TYPE: PRT
<213> ORGANISM: artificial sequence
<220> FEATURE:
<223> OTHER INFORMATION: Aminoacylase 1

<400> SEQUENCE: 35

Pro Asp Val Asp Phe Lys
1               5

<210> SEQ ID NO 36
<211> LENGTH: 7
<212> TYPE: PRT
<213> ORGANISM: artificial sequence
<220> FEATURE:
<223> OTHER INFORMATION: L-FABP

<400> SEQUENCE: 36

Pro Glu Glu Leu Ile Gln Lys
1               5
```

```
<210> SEQ ID NO 37
<211> LENGTH: 11
<212> TYPE: PRT
<213> ORGANISM: artificial sequence
<220> FEATURE:
<223> OTHER INFORMATION: Protein disulfide isomerase

<400> SEQUENCE: 37

Pro Glu Glu Glu Asp His Val Leu Val Leu Arg
1               5                   10

<210> SEQ ID NO 38
<211> LENGTH: 10
<212> TYPE: PRT
<213> ORGANISM: artificial sequence
<220> FEATURE:
<223> OTHER INFORMATION: Protein disulfide isomerase

<400> SEQUENCE: 38

Pro Glu Ser Glu Glu Leu Thr Ala Glu Arg
1               5                   10

<210> SEQ ID NO 39
<211> LENGTH: 8
<212> TYPE: PRT
<213> ORGANISM: artificial sequence
<220> FEATURE:
<223> OTHER INFORMATION: Protein disulfide isomerase

<400> SEQUENCE: 39

His Ile Leu Leu Phe Leu Pro Lys
1               5

<210> SEQ ID NO 40
<211> LENGTH: 5
<212> TYPE: PRT
<213> ORGANISM: artificial sequence
<220> FEATURE:
<223> OTHER INFORMATION: Protein disulfide isomerase

<400> SEQUENCE: 40

Pro Ile Trp Asp Lys
1               5

<210> SEQ ID NO 41
<211> LENGTH: 7
<212> TYPE: PRT
<213> ORGANISM: artificial sequence
<220> FEATURE:
<223> OTHER INFORMATION: Protein disulfide isomerase

<400> SEQUENCE: 41

His Ser Phe Pro Thr Leu Lys
1               5

<210> SEQ ID NO 42
<211> LENGTH: 6
<212> TYPE: PRT
<213> ORGANISM: artificial sequence
<220> FEATURE:
<223> OTHER INFORMATION: Protein disulfide isomerase

<400> SEQUENCE: 42

Pro Ala Ser Ala Asp Arg
1               5
```

```
<210> SEQ ID NO 43
<211> LENGTH: 5
<212> TYPE: PRT
<213> ORGANISM: artificial sequence
<220> FEATURE:
<223> OTHER INFORMATION: Protein disulfide isomerase

<400> SEQUENCE: 43

Pro Glu Tyr Ala Lys
1               5

<210> SEQ ID NO 44
<211> LENGTH: 4
<212> TYPE: PRT
<213> ORGANISM: artificial sequence
<220> FEATURE:
<223> OTHER INFORMATION: Protein disulfide isomerase

<400> SEQUENCE: 44

Pro Ala Val Arg
1

<210> SEQ ID NO 45
<211> LENGTH: 7
<212> TYPE: PRT
<213> ORGANISM: artificial sequence
<220> FEATURE:
<223> OTHER INFORMATION: Keratin, type 1 cytoskeletal 20

<400> SEQUENCE: 45

His Thr Leu Glu Glu Thr Lys
1               5

<210> SEQ ID NO 46
<211> LENGTH: 10
<212> TYPE: PRT
<213> ORGANISM: artificial sequence
<220> FEATURE:
<223> OTHER INFORMATION: Keratin, type 1 cytoskeletal 20

<400> SEQUENCE: 46

Pro Ser Val Tyr Gly Gly Ala Gly Gly Arg
1               5                   10

<210> SEQ ID NO 47
<211> LENGTH: 7
<212> TYPE: PRT
<213> ORGANISM: artificial sequence
<220> FEATURE:
<223> OTHER INFORMATION: 14-3-3 sigma protein

<400> SEQUENCE: 47

Pro Pro Thr Asn Pro Ile Arg
1               5

<210> SEQ ID NO 48
<211> LENGTH: 6
<212> TYPE: PRT
<213> ORGANISM: artificial sequence
<220> FEATURE:
<223> OTHER INFORMATION: S100-A11 protein Calgizarin

<400> SEQUENCE: 48

Pro Thr Glu Thr Glu Arg
1               5

<210> SEQ ID NO 49
```

<211> LENGTH: 6
<212> TYPE: PRT
<213> ORGANISM: artificial sequence
<220> FEATURE:
<223> OTHER INFORMATION: S100-A11 protein Calgizarin

<400> SEQUENCE: 49

Pro Gly Val Leu Asp Arg
1               5

<210> SEQ ID NO 50
<211> LENGTH: 12
<212> TYPE: PRT
<213> ORGANISM: artificial sequence
<220> FEATURE:
<223> OTHER INFORMATION: PSA

<400> SEQUENCE: 50

Leu Ser Glu Pro Ala Glu Leu Thr Asp Ala Val Lys
1               5                   10

<210> SEQ ID NO 51
<211> LENGTH: 152
<212> TYPE: PRT
<213> ORGANISM: artificial sequence
<220> FEATURE:
<223> OTHER INFORMATION: Tp435

<400> SEQUENCE: 51

Met Arg Gly Ser Ala Cys Val Ser Cys Thr Thr Val Cys Pro His Ala
1               5                   10                  15

Gly Lys Ala Lys Ala Glu Lys Val Glu Cys Ala Leu Lys Gly Gly Ile
            20                  25                  30

Phe Arg Gly Thr Leu Pro Ala Ala Asp Cys Pro Gly Ile Asp Thr Thr
        35                  40                  45

Val Thr Phe Asn Ala Asp Gly Thr Ala Gln Lys Val Glu Leu Ala Leu
    50                  55                  60

Glu Lys Lys Ser Ala Pro Ser Pro Leu Thr Tyr Arg Gly Thr Trp Met
65                  70                  75                  80

Val Arg Glu Asp Gly Ile Val Glu Leu Ser Leu Val Ser Ser Glu Gln
                85                  90                  95

Ser Lys Ala Pro His Glu Lys Glu Leu Tyr Glu Leu Ile Asp Ser Asn
            100                 105                 110

Ser Val Arg Tyr Met Gly Ala Pro Gly Ala Gly Lys Pro Ser Lys Glu
        115                 120                 125

Met Ala Pro Phe Tyr Val Leu Lys Lys Thr Lys Lys Gly Ser Ser Lys
    130                 135                 140

Tyr Lys Tyr His His His His
145                 150

<210> SEQ ID NO 52
<211> LENGTH: 428
<212> TYPE: PRT
<213> ORGANISM: artificial sequence
<220> FEATURE:
<223> OTHER INFORMATION: Tp574

<400> SEQUENCE: 52

Met Arg Gly Ser Ala His His Glu Thr His Tyr Gly Tyr Ala Thr Leu
1               5                   10                  15

Ser Tyr Ala Asp Tyr Trp Ala Gly Glu Leu Gly Gln Ser Arg Asp Val
            20                  25                  30

```
Leu Leu Ala Gly Asn Ala Glu Ala Asp Arg Ala Gly Asp Leu Asp Ala
            35                  40                  45

Gly Met Phe Asp Ala Val Ser Arg Ala Thr His Gly His Gly Ala Phe
 50                  55                  60

Arg Gln Gln Phe Gln Tyr Ala Val Glu Val Leu Gly Glu Lys Val Leu
 65                  70                  75                  80

Ser Lys Gln Glu Thr Glu Asp Ser Arg Gly Arg Lys Lys Trp Glu Tyr
                85                  90                  95

Glu Thr Asp Pro Ser Val Thr Lys Met Val Arg Ala Ser Ala Ser Phe
            100                 105                 110

Gln Asp Leu Gly Glu Asp Gly Glu Ile Lys Phe Glu Ala Val Glu Gly
        115                 120                 125

Ala Val Ala Leu Ala Asp Arg Ala Ser Ser Phe Met Val Asp Ser Glu
130                 135                 140

Glu Tyr Lys Ile Thr Asn Val Lys Val His Gly Met Lys Phe Val Pro
145                 150                 155                 160

Val Ala Val Pro His Glu Leu Lys Gly Ile Ala Lys Glu Lys Phe His
                165                 170                 175

Phe Val Glu Asp Ser Arg Val Thr Glu Asn Thr Asn Gly Leu Lys Thr
            180                 185                 190

Met Leu Thr Glu Asp Ser Phe Ser Ala Arg Lys Val Ser Ser Met Glu
        195                 200                 205

Ser Pro His Asp Leu Val Val Asp Thr Val Gly Thr Gly Tyr His Ser
210                 215                 220

Arg Phe Gly Ser Asp Ala Glu Ala Ser Val Met Leu Lys Arg Ala Asp
225                 230                 235                 240

Gly Ser Glu Leu Ser His Arg Glu Phe Ile Asp Tyr Val Met Asn Phe
                245                 250                 255

Asn Thr Val Arg Tyr Asp Tyr Gly Asp Asp Ala Ser Tyr Thr Asn
            260                 265                 270

Leu Met Ala Ser Tyr Gly Thr Lys His Ser Ala Asp Ser Trp Trp Lys
        275                 280                 285

Thr Gly Arg Val Pro Arg Ile Ser Cys Gly Ile Asn Tyr Gly Phe Asp
290                 295                 300

Arg Phe Lys Gly Ser Gly Pro Gly Tyr Tyr Arg Leu Thr Leu Ile Ala
305                 310                 315                 320

Asn Gly Tyr Arg Asp Val Val Ala Asp Val Arg Phe Leu Pro Lys Tyr
                325                 330                 335

Glu Gly Asn Ile Asp Ile Gly Leu Lys Gly Lys Val Leu Thr Ile Gly
            340                 345                 350

Gly Ala Asp Ala Glu Thr Leu Met Asp Ala Ala Val Asp Val Phe Ala
        355                 360                 365

Asp Gly Gln Pro Lys Leu Val Ser Asp Gln Ala Val Ser Leu Gly Gln
370                 375                 380

Asn Val Leu Ser Ala Asp Phe Thr Pro Gly Thr Glu Tyr Thr Val Glu
385                 390                 395                 400

Val Arg Phe Lys Glu Phe Gly Ser Val Arg Ala Lys Val Val Ala Gln
                405                 410                 415

Ser Ser Lys Tyr Lys Thr His His His His His
            420                 425

<210> SEQ ID NO 53
<211> LENGTH: 9
```

```
<212> TYPE: PRT
<213> ORGANISM: artificial sequence
<220> FEATURE:
<223> OTHER INFORMATION: Tp435

<400> SEQUENCE: 53

Ser Ala Pro Ser Pro Leu Thr Tyr Arg
1               5

<210> SEQ ID NO 54
<211> LENGTH: 11
<212> TYPE: PRT
<213> ORGANISM: artificial sequence
<220> FEATURE:
<223> OTHER INFORMATION: Tp574

<400> SEQUENCE: 54

Phe Val Pro Val Ala Val Pro His Glu Leu Lys
1               5                   10
```